United States Patent
Went et al.

(10) Patent No.: US 8,426,472 B2
(45) Date of Patent: *Apr. 23, 2013

(54) METHOD AND COMPOSITION FOR ADMINISTERING AN NMDA RECEPTOR ANTAGONIST TO A SUBJECT

(75) Inventors: Gregory T. Went, Mill Valley, CA (US); Timothy J. Fultz, Pleasant Hill, CA (US); Seth Porter, San Carlos, CA (US); Laurence R. Meyerson, Las Vegas, NV (US); Timothy S. Burkoth, San Francisco, CA (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/284,630

(22) Filed: Oct. 28, 2011

(65) Prior Publication Data

US 2012/0046365 A1 Feb. 23, 2012

Related U.S. Application Data

(60) Continuation of application No. 12/512,701, filed on Jul. 30, 2009, now Pat. No. 8,168,209, which is a division of application No. 11/285,905, filed on Nov. 22, 2005, now Pat. No. 7,619,007, said application No. 12/512,701 is a continuation-in-part of application No. 11/399,879, filed on Apr. 6, 2006, now Pat. No. 8,058, 291, and a continuation-in-part of application No. 11/285,905, filed on Nov. 22, 2005, now Pat. No. 7, 619,007.

(60) Provisional application No. 60/630,885, filed on Nov. 23, 2004, provisional application No. 60/635,365, filed on Dec. 10, 2004, provisional application No. 60/701,857, filed on Jul. 22, 2005, provisional application No. 60/669,290, filed on Apr. 6, 2005.

(51) Int. Cl.
| | |
|---|---|
| A01N 33/02 | (2006.01) |
| A01N 33/18 | (2006.01) |
| A01N 33/24 | (2006.01) |
| A61K 31/13 | (2006.01) |
| A61K 31/04 | (2006.01) |
| A61K 9/22 | (2006.01) |

(52) U.S. Cl.
USPC ............ 514/662; 514/740; 514/964; 424/468

(58) Field of Classification Search .................. 514/662, 514/740, 964; 424/468
See application file for complete search history.

(56) References Cited

U.S. PATENT DOCUMENTS

| | | | |
|---|---|---|---|
| 3,152,180 A | 10/1964 | Haaf | |
| 3,391,142 A | 7/1968 | Mills et al. | |
| 3,992,518 A | 11/1976 | Chien et al. | |
| 4,148,896 A | 4/1979 | Smith et al. | |
| 4,273,774 A | 6/1981 | Scherm | |
| 4,284,444 A | 8/1981 | Bernstein et al. | |
| 4,346,112 A | 8/1982 | Henkel et al. | |
| 4,606,909 A | 8/1986 | Bechgaard et al. | |
| 4,663,318 A | 5/1987 | Davis | |
| 4,767,628 A | 8/1988 | Hutchinson | |
| 4,769,027 A | 9/1988 | Baker et al. | |
| 4,812,481 A | 3/1989 | Reischig et al. | |
| 4,839,177 A | 6/1989 | Colombo et al. | |
| 4,861,800 A | 8/1989 | Buyske | |
| 4,895,841 A | 1/1990 | Sugimoto et al. | |
| 4,897,268 A | 1/1990 | Tice et al. | |
| 4,904,681 A | 2/1990 | Cordi et al. | |
| 4,948,807 A | 8/1990 | Rosin et al. | |
| 5,057,321 A | 10/1991 | Edgren et al. | |
| 5,061,703 A | 10/1991 | Bormann et al. | |
| 5,061,721 A | 10/1991 | Cordi et al. | |
| 5,086,072 A | 2/1992 | Trullas et al. | |
| 5,162,346 A | 11/1992 | Lobisch et al. | |
| 5,186,938 A | 2/1993 | Sablotsky et al. | |
| 5,190,763 A | 3/1993 | Edgren et al. | |
| 5,192,550 A | 3/1993 | Edgren et al. | |
| 5,221,536 A | 6/1993 | Edgren et al. | |
| 5,334,618 A | 8/1994 | Lipton | |
| 5,358,721 A | 10/1994 | Guittard et al. | |
| 5,366,738 A | 11/1994 | Rork et al. | |
| 5,382,601 A | 1/1995 | Numberg et al. | |
| 5,395,626 A | 3/1995 | Kotwal et al. | |
| 5,422,120 A | 6/1995 | Kim | |
| 5,422,123 A | 6/1995 | Conte et al. | |
| 5,484,608 A | 1/1996 | Rudnic et al. | |
| 5,502,058 A | 3/1996 | Mayer et al. | |
| 5,521,178 A | 5/1996 | Nickel et al. | |
| 5,601,845 A | 2/1997 | Buxton et al. | |
| 5,614,560 A | 3/1997 | Lipton | |

(Continued)

FOREIGN PATENT DOCUMENTS

| | | |
|---|---|---|
| AU | 2002323873 B2 | 1/2003 |
| CA | 2323805 A1 | 9/1999 |
| EP | 0350080 | 1/1990 |
| EP | 0392059 A1 | 10/1990 |
| EP | 0451484 A1 | 10/1991 |
| EP | 0488959 A2 | 11/1991 |
| EP | 0488959 A3 | 8/1992 |
| EP | 0502642 A1 | 9/1992 |
| EP | 0524968 | 2/1993 |
| EP | 0733359 | 9/1996 |

(Continued)

OTHER PUBLICATIONS

2006 Chemical Abstracts Service Catalog. Published 2006 by Chemical Abstracts Service, p. 52.

Ambrozi, et al. Treatment of Impaired Cerebral Function in Psychogeriatric Patients with Memantine—Results of a Phase II Double-Blind Study. Pharmacopsychiat. 1988;21(3):144-6.

(Continued)

*Primary Examiner* — Kendra D Carter

(74) *Attorney, Agent, or Firm* — Wilson, Sonsini, Goodrich & Rosati

(57) ABSTRACT

The invention provides methods and compositions for administering an NMDA receptor antagonist (e.g., memantine) to a subject.

10 Claims, 7 Drawing Sheets

U.S. PATENT DOCUMENTS

| | | |
|---|---|---|
| 5,648,087 A | 7/1997 | Ovaert et al. |
| 5,660,848 A | 8/1997 | Moo-Young |
| 5,726,180 A | 3/1998 | Kuriha et al. |
| 5,756,115 A | 5/1998 | Moo-Young et al. |
| 5,891,885 A | 4/1999 | Caruso |
| 5,912,013 A | 6/1999 | Rudnic et al. |
| 5,919,826 A | 7/1999 | Caruso |
| 5,958,919 A | 9/1999 | Olney et al. |
| 6,046,232 A | 4/2000 | Kelleher et al. |
| 6,057,364 A | 5/2000 | Jasys et al. |
| 6,066,652 A | 5/2000 | Zenner et al. |
| 6,114,392 A | 9/2000 | Gilad et al. |
| 6,183,770 B1 | 2/2001 | Muchin et al. |
| 6,187,338 B1 | 2/2001 | Caruso et al. |
| 6,194,000 B1 | 2/2001 | Smith et al. |
| 6,217,905 B1 | 4/2001 | Edgren et al. |
| 6,258,827 B1 | 7/2001 | Chenard et al. |
| 6,284,276 B1 | 9/2001 | Rudnic et al. |
| 6,384,083 B1 | 5/2002 | Ludwig et al. |
| 6,392,104 B1 | 5/2002 | Ishii et al. |
| 6,444,702 B1 | 9/2002 | Wang et al. |
| 6,479,553 B1 | 11/2002 | McCarthy |
| 6,491,949 B2 | 12/2002 | Faour et al. |
| 6,500,454 B1 | 12/2002 | Percel et al. |
| 6,620,845 B2 | 9/2003 | Wang et al. |
| 6,635,268 B2 | 10/2003 | Peery et al. |
| 6,648,083 B2 | 11/2003 | Evans et al. |
| 6,662,845 B1 | 12/2003 | Palmer |
| 6,715,485 B1 | 4/2004 | Djupesland |
| 6,717,012 B2 | 4/2004 | Wang et al. |
| 6,743,211 B1 | 6/2004 | Prausnitz et al. |
| 6,746,689 B2 | 6/2004 | Fischer et al. |
| 6,764,697 B1 | 7/2004 | Jao et al. |
| 6,770,295 B1 | 8/2004 | Kreilgard et al. |
| 6,797,283 B1 | 9/2004 | Edgren et al. |
| 6,852,889 B2 | 2/2005 | Wang et al. |
| 6,913,768 B2 | 7/2005 | Couch et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,930,128 B2 | 8/2005 | D'Amato et al. |
| 6,939,556 B2 | 9/2005 | Lautenbach |
| 6,945,952 B2 | 9/2005 | Kwon |
| 7,619,007 B2 | 11/2009 | Went et al. |
| 8,058,291 B2 | 11/2011 | Went et al. |
| 2002/0035105 A1 | 3/2002 | Caruso |
| 2002/0071863 A1 | 6/2002 | Dong et al. |
| 2003/0190354 A1 | 10/2003 | Sela |
| 2003/0198683 A1 | 10/2003 | Li et al. |
| 2003/0203055 A1 | 10/2003 | Rao et al. |
| 2004/0087658 A1 | 5/2004 | Moebius |
| 2004/0102525 A1 | 5/2004 | Kozachuk |
| 2004/0122090 A1 | 6/2004 | Lipon |
| 2004/0224020 A1 | 11/2004 | Schoenhard |
| 2004/0254251 A1 | 12/2004 | Firestone et al. |
| 2005/0020319 A1 | 1/2005 | Kim et al. |
| 2005/0031651 A1 | 2/2005 | Gervais et al. |
| 2005/0065219 A1 | 3/2005 | Lipton et al. |
| 2005/0124701 A1 | 6/2005 | Went et al. |
| 2005/0153953 A1 | 7/2005 | Trippodi-Murphy et al. |
| 2005/0191349 A1 | 9/2005 | Boehm et al. |
| 2005/0203191 A1 | 9/2005 | McDonald et al. |
| 2005/0208132 A1 | 9/2005 | Sathyan et al. |
| 2005/0209218 A1 | 9/2005 | Meyerson |
| 2005/0232990 A1 | 10/2005 | Boehm et al. |
| 2005/0245460 A1 | 11/2005 | Meyerson |
| 2005/0245617 A1 | 11/2005 | Meyerson et al. |
| 2005/0267176 A1 | 12/2005 | Barberich |
| 2006/0002999 A1 | 1/2006 | Yang et al. |
| 2006/0020042 A1 | 1/2006 | McDonald et al. |
| 2006/0051416 A1 | 3/2006 | Rastogi et al. |
| 2006/0052370 A1 | 3/2006 | Meyerson |
| 2006/0062851 A1 | 3/2006 | Vergez et al. |
| 2006/0063810 A1 | 3/2006 | Vergez et al. |
| 2006/0079578 A1 | 4/2006 | Laurin et al. |
| 2006/0142398 A1 | 6/2006 | Went et al. |
| 2006/0159763 A1 | 7/2006 | Meyer et al. |
| 2006/0160852 A1 | 7/2006 | Kimura et al. |
| 2006/0189694 A1 | 8/2006 | Went et al. |
| 2006/0198884 A1 | 9/2006 | Yang et al. |
| 2006/0240043 A1 | 10/2006 | Meyerson |
| 2006/0246003 A1 | 11/2006 | Kimura et al. |
| 2006/0252788 A1 | 11/2006 | Went et al. |
| 2007/0065512 A1 | 3/2007 | Dedhiya et al. |
| 2008/0260825 A1 | 10/2008 | Quik et al. |
| 2008/0279819 A1 | 11/2008 | Went et al. |
| 2010/0022659 A1 | 1/2010 | Meyerson |
| 2010/0047342 A1 | 2/2010 | Went et al. |
| 2010/0137448 A1 | 6/2010 | Lipon et al. |
| 2010/0260838 A1 | 10/2010 | Went et al. |
| 2010/0266684 A1 | 10/2010 | Went et al. |
| 2010/0311697 A1 | 12/2010 | Went et al. |
| 2011/0059169 A1 | 3/2011 | Went et al. |
| 2011/0064804 A1 | 3/2011 | Went et al. |

FOREIGN PATENT DOCUMENTS

| | | |
|---|---|---|
| EP | 0870757 A2 | 10/1998 |
| EP | 0927711 A1 | 7/1999 |
| EP | 0870757 A3 | 6/2000 |
| EP | 0452484 B2 | 7/2004 |
| EP | 1559418 | 8/2005 |
| EP | 1600156 | 11/2005 |
| EP | 1832298 A1 | 9/2007 |
| EP | 1509232 B1 | 11/2008 |
| FR | 2219159 | 9/1974 |
| GB | 1173492 A | 12/1969 |
| JP | 58-4718 | 1/1983 |
| JP | 10203966 A | 8/1998 |
| WO | WO 89/09051 A1 | 10/1989 |
| WO | WO 91/06291 A1 | 5/1991 |
| WO | WO 91/14445 A1 | 10/1991 |
| WO | WO-92-17168 | 10/1992 |
| WO | WO 94/05275 A1 | 3/1994 |
| WO | WO 94/06428 A1 | 3/1994 |
| WO | WO 95/13796 A1 | 5/1995 |
| WO | WO-97-02273 | 1/1997 |
| WO | WO-97-03670 | 2/1997 |
| WO | WO 97/14415 A1 | 4/1997 |
| WO | WO-98-07447 | 2/1998 |
| WO | WO 98/18457 A1 | 3/1998 |
| WO | WO-98-15275 | 4/1998 |
| WO | WO 98/27961 A2 | 7/1998 |
| WO | WO 98/27961 A3 | 9/1998 |
| WO | WO-98-50044 | 11/1998 |
| WO | WO-00-00197 | 1/2000 |
| WO | WO-00-03716 | 1/2000 |
| WO | WO 00/18378 A1 | 4/2000 |
| WO | WO-00-29023 | 5/2000 |
| WO | WO-00-54810 | 9/2000 |
| WO | WO 00/56301 A2 | 9/2000 |
| WO | WO 00/56301 A3 | 12/2000 |
| WO | WO-01-08682 | 2/2001 |
| WO | WO 01/19901 A2 | 3/2001 |
| WO | WO 01/32115 A1 | 5/2001 |
| WO | WO 01/32148 A1 | 5/2001 |
| WO | WO 01/46291 A1 | 6/2001 |
| WO | WO 01/62706 A1 | 8/2001 |
| WO | WO 01/19901 A3 | 9/2001 |
| WO | WO-01-91753 | 12/2001 |
| WO | WO-03-094812 | 11/2003 |
| WO | WO 03/101458 A1 | 12/2003 |
| WO | WO 2004/012700 A2 | 2/2004 |
| WO | WO 2004/012700 A3 | 4/2004 |
| WO | WO 2004/037234 A2 | 5/2004 |
| WO | WO-2004-056335 | 7/2004 |
| WO | WO 2004/056335 A2 | 7/2004 |
| WO | WO 2004/037234 A3 | 8/2004 |
| WO | WO-2004-087116 | 10/2004 |
| WO | WO 2004/087116 A2 | 10/2004 |
| WO | WO 2004/056335 A3 | 11/2004 |
| WO | WO 2004/087116 A3 | 12/2004 |
| WO | WO 2004/112768 A1 | 12/2004 |
| WO | WO-2005-058420 | 6/2005 |
| WO | WO 2005/065645 A2 | 7/2005 |
| WO | WO 2005/072705 A1 | 8/2005 |
| WO | WO-2005-079773 | 9/2005 |
| WO | WO 2005/079773 A2 | 9/2005 |

| WO | WO-2005-079779 | 9/2005 |
| WO | WO-2005-084655 | 9/2005 |
| WO | WO 2005/065645 A3 | 10/2005 |
| WO | WO 2005/079773 A3 | 10/2005 |
| WO | WO 2005/092009 A2 | 10/2005 |
| WO | WO 2006/009769 A1 | 1/2006 |
| WO | WO 2005/092009 A3 | 2/2006 |
| WO | WO 2006/070781 A1 | 7/2006 |
| WO | WO 2006/089494 A1 | 8/2006 |
| WO | WO 2006/138227 A1 | 12/2006 |

OTHER PUBLICATIONS

Avery's Drug Treatment: Principles and Practice of Clinical Pharmacology and Therapeutics, 3rd Edition, 1987, edited by Trevor M. Speight, Chapter VIII, pp. 255-282.
Barth, et al. Combination therapy with MK-801 and alpha-phenyl-tert-butyl-nitrone enhances protection against ischemic neuronal damage in organotypic hippocampal slice cultures. Exp Neurol. 1996;141(2):330-6.
Bayerl, et al. Klinsche Vergleichsstudie der Antispastika Memantin und Baclofen. (Clinical Comparative Study of the Antispastic Compounds Memantine and Baclofen). Therapiewozhe 1985;35: 5440-5444. (with English abstract).
Beers, M.H. and Berkow, R. Editors-in-chief, The Merck Manual of Diagnosis and Therapy, 17th Edition, pp. 1525-1544,1999.
Bentue-Ferrer, et al. Medication in Alzheimer's disease, Rev. Geriatr. 26(6):511-522 (2001), (in French with English summary).
Berman, et al. Antidepressant effects of ketamine in depressed patients. Biol. Psychiatry. 2000;47:351-354.
Bhat, et al. Localization of the N-methyl-D-aspartate R1 receptor subunit in specific anterior pituitary hormone cell types of the female rat. Neuroendocrinol. 1995;62(2):178-186.
Bliss, et al. A synaptic model of memory: long-term potentiation in the hippocampus. Nature. 1993;361:31-39.
Bormann, J. Memantine is a potent blocker of N-methyl-D-aspartate (NMDA) receptor channels. Eur. J. Pharmacol. 1989;166:591-592.
Braga, et al. Making crystals from crystals: a green route to crystal engineering and polymorphism, Chemical Communications pp. 3635-3645 (2005).
Bredt, et al. Localization of nitric oxide synthase indicating a neural role for nitric oxide. Nature. 1990;347:768-770.
Budziszewska, et al. Antidepressant drugs inhibit glucocorticoid receptor-mediated gene transcription—a possible mechanism. Br J Pharmacol. Jul. 2000;130(6):1385-93.
Bull, Drug review—Memantine, Drugs in Context 2005, I(I):1-40.
Cacabelos, et al. Pharmacological treatment of Alzheimer disease: From psychotropic drugs and cholinesterase inhibitors to pharmacogenomics. Drugs Today. 2000; 36(7):415-499.
Calbabrese, et al. A double-blind placebo-controlled study of lamotrigine monotherapy in outpatients with bipolar I depression. Lamictal 602 Study Group. J. Clin. Psychiatry. 1993;60:79-88.
Camps, et al. Cholinergic drugs in pharmacotherapy of Alzheimer's disease. Mini Rev Med Chem. Feb. 2002;2(1):11-25.
Chamulitrat, et al. Nitric oxide formation during light-induced decomposition of phenyl N-tert-butylnitrone. J. Biol. Chem. 1993; 268(16):11520-11527.
Chen, et al. Mechanism of memantine block of NMDA-activated channels in rat retinal ganglion cells: uncompetitive antagonism. J. Physiol. 1997; 499(1):27-46.
Chen, et al. Neuroprotective concentrations of the N-methyl-D-aspartate open-channel blocker memantine are effective without cytoplasmic vacuolation following post-ischemic administration and do not block maze learning or long-term potentiation. Neurosci. 1998;86(4):1121-1132.
Chen, et al. Open-channel block of N-methyl-D-aspartate (NMDA) responses by memantine: therapeutic advantage against NMDA receptor-mediated neurotoxicity. J. Neurosci. 1992;12(11):4427-4436.
Choi, DW. Glutamate neurotoxicity and diseases of the nervous system. Neuron. 1988;1:623-634.
Chung, et al. Clinical pharmacokinetics of doxazosin in a controlled-release gastrointestinal therapeutic system (GITS) formulation, Br J Clin Pharmacol 1999, 48:678-87.
Cohan, et al. Electrically and chemically mediated increases in intracellular calcium in neuronal growth cones. J. Neurosci. 1987;7(11):3588-3599.
Connor, et al. Depolarization- and transmitter-induced changes in intracellular Ca2+ of rat cerebellar granule cells in explant cultures. J. Neurosci. 1987;7(5):1384-1400.
Connor, et al. Sustained dendritic gradients of Ca2+ induced by excitatory amino acids in CA1 hippocampal neurons. Science. 1988;240(4852):649-53.
Cummings, J. L. Depression and Parkinson's Disease: A Review. The American Journal of Psychiatry. 1992;149(4): 443-454.
Cutler, RG. Human longevity and aging: possible role of reactive oxygen species. Ann. New York Acad. Sci. 1991;621:1-28.
Danysz, et al. Aminoadamantanes as NMDA receptor antagonists and antiparkinsonian agents—preclinical studies. Neurosci. Biobehav. Rev. 1997;21(4):455-468.
Danysz, et al. Memantine provides neuroprotection in animal models at therapeutically relevant doses. Abstracts from the 8th International Conference on Alzheimer's Disease and Related Disorders. Stockholm, Sweden. Jul. 20-25, 2002. No. 297.
Ditzler, K. Efficacy and Tolerability of Memantine in Patients with Dementia Syndrome, Arnzneim.-Forsch./Drug Res. 41 (II), Nr. 8, 773-780 (1991), Bad Krozingen, Germany.
Dooley, et al. Donepezil: A review of its use in Alzheimer's Disease, Drugs and Aging 16(3):199-226 (2000).
Dreyer, et al. HIV-1 coat protein neurotoxicity prevented by calcium channel antagonists. Science. 1990;248:364-367.
Edamatsu, et al. The spin-trap N-tert-alpha-phenyl-butylnitrone prolongs the life span of the senescence accelerated mouse. Biochem. Biophys. Res. Commun. 1995;211(3):847-849.
Edwards, K.R. New Studies on the Pharmacologic Treatment of Painful Neuropathies, Especially in Painful Diabetic Polyneuropathy, 52nd Annual Meeting of the American Academy of Neurology, Apr. 29-May 6, 2000, San Diego, CA, http://www.medscape.com/viewarticle/420246.
Eisenberg, et al. The effects of the clinically tested NMDA receptor antagonist memantine on carrageenan-induced thermal hyperalgesia in rats. Eur. J. Pharmacol. 1994;255(1-3):123-9.
Eisenberg, et al. The NMDA antagonist Memantine blocks pain behavior in a rat model of formalin-induced facial pain. Pain. 1993;54(3):301-7.
European search report dated Oct. 15, 2007 for Application No. 07000173.0.
European Search Report for EP 01 99 0191, mailed May 26, 2004.
FDA Medical Review for Namenda.RTM. NDA 21-487, Oct. 2, 2003, pp. 1-113.
Feldman, et al. A 24-Week, randomized double-blind study of donepezil in moderate to severe Alzheimer's Disease, Neurology 57:613-20 (2001).
Fischer, et al. The effect of intravenous administration of memantine in parkinsonian patients (author's translation). Arzneimit-telforschung. 1977;27(7):1487-1489 (in German with English).
Fleischhacker, et al. Memantine in the treatment of senile dementia of the Alzheimer type. Prog.Prog Neuropsychopharmacol Biol Psychiatry. 1986;10(1):87-93.
Forstl, H. Symptomatic therapy of Alzheimer dementia. Wien Med Wochenschr. 2002;152(3-4):77-80 (in German with English translation).
Foster, et al.Neurobiology. Taking apart NMDA receptors. Nature. 1987;329(6138):395-6.
Fox, et al. Memantine combined with an acetyl cholinesterase inhibitor—hope for the future? Neuropsychiatr Dis Treat. Jun. 2006;2(2):121-5.
Fuchsberger, et al. Starting Alzheimer therapy in early stages whenever possible. Activities of daily living remain intact longer, MMW Fortschr Med., 144(20):36-9 (2002); (in German with English summary).
Galli, et al. Acetylcholinesterase inhibition and protection by dizocilpine (MK-801) enantiomers. J Pharm Pharmacol. Jan. 1996;48(1):71-6.
Garthwaite, et al. Endothelium-derived relaxing factor release on activation of NMDA receptors suggests role as intercellular messenger in the brain. Nature. 1988;336(6197):385-8.

Gauthier, et al. Effects of memantine on behavioural symptoms in Alzheimer's disease patients: an analysis of the Neuropsychiatric Inventory (NPI) data of two randomised, controlled studies. Int J Geriatr Psychiatry. May 2005;20(5):459-64.

Gauthier, et al. Functional, Cognitive, and Behavioral Effects of Donepezil in Patients with Moderate Alzheimer's Disease, Current Medical Research and Opinion® 18(6):347-54 (2002).

Gelvan, et al. Cardiac reperfusion damage prevented by a nitroxide free radical. Proc. Natl. Acad. Sci. USA. 1991;88(11):4680-4.

Gortelmeyer, et al., Memantine in the Treatment of Mild to Moderate Dementia Syndrome, Arnzneim.-Forsh./Drug Res. 42 (II), Nr. 7, 904-913 (1992), Frankfurt, Germany.

Graham, et al. Plasma homocysteine as a risk factor for vascular disease. The European Concerted Action Project.JAMA. 1997 277(22):1775-1781.

Greenberg, et al. Treatment of Major Depression and Parkinson's Disease with Combined Phenelzine and Amantadine. Am. J. Psychiatry. 1985;142(2):273-274.

Greene, T.W. Protective Groups in Organic Synthesis. John Wiley & Sons, pp. 70-71 (1981).

Grossmann, et al. Memantine and neurogenic bladder disorders in spastic clinical pictures, Arzneim.-Forsch./Drug Res. 1982, 32(II)(10):1273-6. (in German with English Summary).

Grynkiewicz, et al. A new generation of Ca2+ indicators with greatly improved fluorescence properties. J. Biol. Chem. 1985;260(6):3440-3450.

Gupta, et al. Novel effects of memantine in antagonizing acute aldicarb toxicity: Mechanistic and applied considerations. Drug development research. 1991; 24:329-341.

Gupta, et al. Prevention and antagonism of acute carbofuran intoxication by memantine and atropine. J Toxicol Environ Health. 1989;28(1):111-22.

Hahn, et al. Central mammalian neurons normally resistant to glutamate toxicity are made sensitive by elevated extracellular Ca2+: toxicity is blocked by the N-methyl-D-aspartate antagonist MK-801. Proc. Natl. Acad. Sci. USA. 1998;;85(17):6556-60.

Hartmann, et al. Tolerability of memantine in combination with cholinesterase inhibitors in Alzheimer's disease and vascular dementia. Abstracts from the 8th International Conference on Alzheimer's Disease and Related Disorders. Stockholm, Sweden. Jul. 20-25, 2002. No. 317.

Hartmann, et al. Tolerability of memantine in combination with cholinesterase inhibitors in dementia therapy. Int. Clin. Physchopharmacol, 2003, 18(2):81-85.

Helmuth, L. New Alzheimer's treatments that may ease the mind. Science. Aug. 23, 2002;297(5585):1260-2.

Ho, et al. Memantine: A New Treatment Option for Patients with Moderate-to-Severe Alzheimer's Disease. P&T, vol. 29 No. 3, Mar. 2004.

Hoffmann, et al. Eight-year prescription trends of memantine and cholinesterase inhibitors among persons 65 years and older in Germany. Int Clin Psychopharmacol. Jan. 2010;25(1):29-36.

Ihl, R. Dementing disorders. What benefits do the new anti-dementia drugs have? MMW Fortschr Med. May 6, 2002;Suppl 2:24-6, 28-9 (in German with English translation).

Jain, et al. Evaluation of memantine for neuroprotection in dementia, Exp. Opin. Invest. Drugs, 2000, 9(6):1-10.

Jain, et al. Polymorphism in Pharmacy, Indian Drugs 23(6):315-29 (1986).

Jain, K.K. Evaluation of memantine for neuroprotection in dementia. Expert Opin Investig Drugs. Jun. 2000;9(6):1397-406.

Janzen, et al. Stabilities of hydroxyl radical spin adducts of PBN-type spin traps. Free Rad. Biol. Med. 1992;12(2):169-73.

Johnson, et al. Neuropharmacology of phencyclidine: basic mechanisms and therapeutic potential. Annu. Rev. Pharmacol. Toxicol. 1990; 30:707-750.

Karcz-Kubicha, et al. Anxiolytic activity of glycine-B antagonists and partial agonists—no relation to intrinsic activity in the patch clamp. Neuropharmacol. 1997;36(10):1355-67.

Keilhoff, et al. Memantine prevents quinolinic acid-induced hippocampal damage. Eur. J. Pharmacol. 1992;219:451-454.

Klockgether, et al. Excitatory amino acids and the basal ganglia: implications for the therapy of Parkinson's disease. Trends Neurosci. 1989;12(8):285-286.

Klockgether, et al. NMDA antagonists potentiate antiparkinsonian actions of L-dopa in monoamine-depleted rats. Ann Neurol. Oct. 1990;28(4):539-46.

Kornhuber, et al. Amantadine and Memantine are NMDA receptor antagonists with neuroprotective properties. J Neural Transm Suppl. 1994;43:91-104.

Kornhuber, et al. Cerebrospinal fluid and serum concentrations of the N-methyl-D-aspartate (NMDA) receptor antagonist memantine in man. Neurosci. Lett. 1995;195(2):137-9.

Kornhuber, et al. Effects of the 1-amino-adamantanes at the MK-801-binding site of the NMDA-receptor-gated ion channel: a human postmortem brain study. Eur J. Pharmacol. 1991;206(4):297-300.

Kornhuber, et al. Memantine displaces [3H]MK-801 at therapeutic concentrations in postmortem human frontal cortex. Eur. J. Pharmacol. 1989;166(3):589-90.

Kotake, et al. Decay and Fate of the Hydroxyl Radical Adduct of .alpha.-Phenyl-N-tert-butylnitrone in Aqueous Media. J. Am. Chem. Soc. 1991;113:9503-9506.

Krishna, et al. Do nitroxide antioxidants act as scavengers of O2-. Or as SOD mimics? J Biol. Chem. 1996;271(42):26026-31.

Krishna, et al.Stimulation by nitroxides of catalase-like activity of hemeproteins. Kinetics and mechanism. J. Biol. Chem. 1996;271(42):26018-26025.

Leskow, P. Therapie zentral bedingter Bewegungsstorungen: Multicenterstudie mit memantine. Therapiewoche 1987;37:4843-4845.

Letter from British Library dated Aug. 11, 2008 re MMW Fortschritte.

Levy, et al. Comparison of delayed administration of competitive and uncompetitive antagonists in preventing NMDA receptor-mediated neuronal death. Neurol. 1990;40:852-855.

Levy, et al. Redox modulation of NMDA receptor-mediated toxicity in mammalian central neurons. Neurosci. Lett. 1990;110:291-296.

Li, et al. Memantine restores the oka daic acid-induced changes in the activities of protein phosphatase-2a and calcium, calmodulin-protein kinase II and hyperphosphorylation of tau in rat hippocampal slices in culture. Abstracts from the 8th International Conference on Alzheimer's Disease and Related Disorders. Stockholm, Sweden. Jul. 20-25, 2002. No. 421.

Li, et al. Pharmacological reversal of behavioral and cellular indices of cocaine sensitization in the rat. Psychopharmacology (Berl). Aug. 2000;151(2-3):175-83.

Lipton, SA. Prospects for clinically tolerated NMDA antagonists: open-channel blockers and alternative redox states of nitric oxide. Trends Neurosci. 1993;16(12):527-532.

Loveman, et al. Health Technology Assessment. 2006; vol. 10, No. 1 (extract).

Maj, von J. Arzneim-Forsch/Drug Res., 32(10): 1256-1259 (1982) (in German, with Summary in English only).

Masuo, et al. Effects of memantine on the frog neuromuscular junction.Eur. J. Pharmacol. 1986;130(3):187-195.

Mattson, et al. Fibroblast growth factor and glutamate: opposing roles in the generation and degeneration of hippocampal neuroarchitecture. J. Neurosci. 1989;9(11):3728-3740.

Mayer, et al. Excitatory amino acid receptors, second messengers and regulation of intracellular Ca2+ in mammalian neurons. Trends Pharmacol. Sci. 1990;11:254-260.

Mayeux, et al. Treatment of Alzheimer's disease. N. Engl. J. Med. 1999; 341(22):1670-1679.

McCully, K.S. Vascular pathology of homocysteinemia: implications for the pathogenesis of arteriosclerosis. Am. J. Pathol. 1969;56(1):111-128.

McDonald, et al. Physiological and pathophysiological roles of excitatory amino acids during central nervous system development. Brain Res Brain Res Rev. Jan.-Apr. 1990;15(1):41-70.

McLean, et al. Prophylactic and therapeutic efficacy of memantine against seizures produced by soman in the rat. Toxicol Appl Pharmacol. Jan. 1992;112(1):95-103.

Merello, et al. Effect of memantine (NMDA antagonist) on Parkinson's disease: a double-blind crossover randomized study. Clin. Neuropharmacol. 1999;22(5):273-276.

Miguel-Hidalgo, et al. Memantine prevents β-amyloid-induced neurotoxicity and learning impairment in rats. Abstracts from the 8th International Conference on Alzheimer's Disease and Related Disorders. Stockholm, Sweden. Jul. 20-25, 2002. No. 385.

Miltner, F.O. Utility of symptomatic therapy with memantine in cerebral coma. Arzneimittelforschung, 32(10):1271-1273 (1982) (in German, with English).

Mohsen, et al. Do nitroxides protect cardiomyocytes from hydrogen peroxide or superoxide? Mol. Cell. Biochem.1995;145(2): 103-110.

Montgomery, et al. Profiles of Antidepressant Activity with the Montgomery-Asberg Depression Rating Scale. Acta Psychiatr Scand Suppl. 1985; 320:38-42.

Moryl, et al. Potential antidepressive properties of amantadine, memantine and bifemelane. Pharmacol. Toxicol. 1993;72(6):394-397.

Murray, et al. A facile one-step synthesis of C-arylnitrones using dimethyldioxirane. J. Org. Chem. 1990; 55:2954-2957.

Namenda label, NDA 21-487, pp. 1-20. 2007. Forest Pharmaceuticals, Inc.

Nikolajsen, et al. Memantine (a N-methyl-D-aspartate receptor antagonist) in the treatment of neuropathic pain after amputation or surgery: a randomized, double-blinded, cross-over study. Anesth. Analg. 2000;91:960-966.

Nilsson, et al. Increased Rick of Developing Parkinson's Disease for Patients with Major Affective Disorder: A Register Study. Acta Psychiatr Scand, 2001; 104:380-386.

Nowak, et al. Alterations in the N-methyl-D-aspartate (NMDA) receptor complex in the frontal cortex of suicide victims. Brain Res. 1995;675:157-164.

Nygard, et al. Plasma homocysteine levels and mortality in patients with coronary artery disease. N. Engl. J. Med. 1997;337(4):230-236.

Opposition by Adamas Pharmaceuticals, Inc. against the grant of European Patent 1509232 B1 in the name of H. Lundbeck A/S dated Aug. 19, 2009.

Orgogozo, et al. Efficacy and Safety of Memantine in Patients with Mild to Moderate Vascular Dementia. A Randomized, Placebo-Controlled Trial (MMM 300), Stroke. 2002; 33(7):1834-9.

Ossowska, et al. The effect of NMDA antagonists on footshock-induced fighting behavior in chronically stressed rats. J. Physiol. Pharmacol. 1997;48(1):127-135.

Pantev, et al. Clinical and Behavioural Evaluation in Long-Term Care Patients with Mild to Moderate Dementia Under Memantine Treatment. Zeitschrift fur Gerontopsychologie and psychiatric, 6 (1993) Heft 2, S. 103-117.

Parsons, et al. Memantine is a clinically well tolerated N-methyl-D-aspartate (NMDA) receptor antagonist—a review of preclinical data. Neuropharmacology, 38:735-767 (1999).

Paul, et al. Adaptation of the N-methyl-D-aspartate receptor complex following chronic antidepressant treatments. J. Pharmacol. Exp. Ther. 1994;269(1):95-102.

Periclou, et al. Lack of pharmacokinetic or pharmacodynamic interaction between memantine and donepezil. Ann. Pharmacother, 2004, 38(9):1389-94.

Pharmaceutical Dosage Forms: Tablets, Second Edition, Revised and Expanded, published by Marcel Dekker, Inc., edited by Lieberman, Lachman, and Schwartz. 1990; pp. 462-472.

Popik, et al. Chronic treatment with antidepressants affects glycine/NMDA receptor function: behavioral evidence. Neuropharmacol. 2000;39:2278-2287.

Popik, et al. The NMDA antagonist memantine blocks the expression and maintenance of morphine dependence. Pharmacol. Biochem. Behavior 1996;53(4):791-797.

Rabey, et al. Efficacy of Memantine, an NMDA Receptor Antagonist, in the Treatment of Parkinson's Disease. J Neural Transm. 1992; 4:277-82.

Rammes, et al. The N-methyl-D-aspartate receptor channel blockers memantine, MRZ 2/579 and other amino-alkyl-cyclohexanes antagonise 5-HT(3) receptor currents in cultured HEK-293 and N1E-115 cell systems in a non-competitive manner. Neuroscience Letters, 306(1-2):81-84, Jun. 22, 2001.

Rausch, et al. Effects of L-deprenyl and amantadine in an MPTP-model of parkinsonism. J. Neural Transm. 1990;32:269-275.

Reisberg, et al. Long-term treatment with the NMDA antagonist memantine: results of a 24-week, open-label extension study in moderately severe-to-severe Alzheimer's disease. Abstracts from the 8th International Conference on Alzheimer's Disease and Related Disorders. Stockholm, Sweden. Jul. 20-25, 2002. No. 2039.

Reisberg, et al. Memantine in moderate-to-severe alzheimer's disease, N. Eng. J. Med. 2003; 348(14):1333-1341.

Reiser, et al. Memantine (1-amino-3,5-dimethyladamantane) blocks the serotonin-induced depolarization response in a neuronal cell line. Brain Res. 1988;443(1-2):338-44.

Riederer, et al. Pharmacotoxic psychosis after memantine in Parkinson's disease. Lancet. 1991;338:1022-1023.

Rieke, et al. Effectiveness and tolerance of memantine in patients with dementia. Die Medizinische Welt, 47:251-254 (1996) (in German with English).

Sack, et al. Antioxidant treatment with phenyl-alpha-tert-butyl nitrone (PBN) improves the cognitive performance and survival of aging rats. Neurosci. Lett. 1996;205(3):181-184.

Samuni, et at. A novel metal-free low molecular weight superoxide dismutase mimic. J. Biol. Chem. 1988;263(34):17921-17924.

Sansom, L.R. Oral extended-release products. Aust Prescr 1999, 22:88-90.

Schmidt, et al. Excitatory amino acids and Parkinson's disease. Trends Neurosci. 1990;13(2):46-47.

Schneider, et al. Effects of oral memantine administration on Parkinson symptoms. Results of a placebo-controlled multicenter study .Dtsch. Med. Wschr. 1984;109(25):987-990. (in German with English abstract).

Schulz, et al. The use of diurnal vigilance changes in the EEG to verify vigilance-enhancing effects of memantine in a clinical pharmacological study. Neuropsychobiol. 1996;33(1):32-40.

Schwab, et al. Amantadine in the treatment of Parkinson's disease. JAMA. May 19, 1969;208(7):1168-70.

Semenova, et al. Low-affinity NMDA receptor channel blockers inhibit acquisition of intravenous morphine self-administration in naive mice. Eur. J. Pharmacol. Jul. 28, 1999;378(1):1-8.

Siemers, E. Recent progress in the treatment of Parkinson's disease. Comprehensive Therapy. 1992; 18(9):20-24.

Silverman, R. The Organic Chemistry of Drug Design and Drug Action, published 1992 by Academic Press, pp. 19-21 and 352-397.

Skolnick, P. Antidepressants for the new millennium. J. Pharmacol. 1999;375(1-3):31-40.

Smith, et al. Models for studying long-term recovery following forebrain ischemia in the rat. 2. A 2-vessel occlusion model. ACTA Neurol. Scand. 1984;69(6):385-401.

Sviridov, et al. C-hydroxyalkylation of N-adamantylanilines by hexafluoroacetone and methyl trifluoropyruvate. Izv. Akad. Nauk SSSR, Ser. Khim. 1989; 10:2348-2350 (English translation).

Tal, M. A novel antioxidant alleviates heat hyperalgesia in rats with an experimental painful peripheral neuropathy. Neuroreport. May 31, 1996;7(8):1382-4.

Tariot, et al. Memantine treatment in patients with moderate to severe Alzheimer disease already receiving donepezil: a randomized controlled trial. JAMA, 2004, 291(3):317-324.

The Merck Manual of Diagnosis and Therapy, 17th Edition, published 1999 by Merck Research Laboratories, pp. 1393-1400.

Third Party Submission in Published Application Under 37 C.F.R.1.99 dated Apr. 20, 2010 regarding U.S. Appl. No. 12/512,701, filed Jul. 30, 2009. 149 pages.

Upchurch, et al. Homocyst(e)ine decreases bioavailable nitric oxide by a mechanism involving glutathione peroxidase.J. Biol. Chem. 1997;272(27):17012-17017.

Vale, et al. Amantadine in depression. Lancet. 1971; 11:437.

Vippagunta, et al. Crystalline Solids, Advanced Drug Delivery Reviews 48:3-26 (2001).

Walder, et al. Cognitive functioning, cortisol release, and symptom severity in patients with schizophrenia. Biol. Psychiatry. 2000;48(12):1121-1132.

Walsh, et al. Parkinson's Disease and Anxiety. Postgraduate Medical Journal, Feb. 2001; 77:89-93.

Wenk, et al. No interaction of memantime with acetylcholinesterase inhibitors approved for clinical use. Life Sci. 2000, 66(12):1079-83.

Wesemann, et al. Distribution of metabolism of the potential antiparkinson drug memantine in the human. J. Neural Transm. Suppl. 1980;16:143-148.

Wilcock, et al. A Double-Blind, Placebo-Controlled Multicentre Study of Memantine in Mild to Moderate Vascular Dementia (MMM500). Int Clin Psychopharmacol. 2002; 17(6):297-305.

Williams, et al. Calcium gradients in single smooth muscle cells revealed by the digital imaging microscope using Fura-2. Nature. 1985; 318:558-561.

Wilson, et al. Combination drug regimens hold great promise for Alzheimer treatment. Science Blog. Available at http://www.scienceblog.com/community/older/archives/K/5/pub5611.html. Accessed Jan. 29, 2010.

Wimo, et al. Effect of long-term treatment with memantine, and nmda antagonist on costs associated with advanced Alzheimer's disease: results of a 28-week, randomized, double-blind, placebo-controlled study. Abstracts from the 8th International Conference on Alzheimer's Disease and Related Disorders. Stockholm, Sweden. Jul. 20-25, 2002. No. 167.

Wimo, et al. Pharmacoeconomics and dementia. Abstracts from the 8th International Conference on Alzheimer's Disease and Related Disorders. Stockholm, Sweden. Jul. 20-25, 2002. No. 541.

Winblad, et al. Memantine in Severe Dementia: Results of the 9M-Best Study (Benefit and Efficacy in Severly Demented Patients During Treatment with Memantine). Int. J. Geriat. Psychiatry. 1999; 14:135-146. John Wiley & Sons, Ltd.

Yamada, el at. Changes in symptoms and plasma homovanillic acid with amantadine hydrochloride in chronic schizophrenia. Biol Psychiatry. May 15, 1997;41(10):1062-4.

Yang Hong-Ju, et al. Effect of gabapentin derivates on mechanical allodynia-like behaviour in a rat model of chronic sciatic constriction injury. Bioorganic and Medicinal Chemistry Letters 2004;14:2537-41.

Ziemann, et al. Pharmacological control of facilitatory I-wave interaction in the human motor cortex. A paired transcranial magnetic stimulation study. Electroencephalogr. Clin. Neurophysiol. 1998;109(4):321-330.

European search report dated Jun. 10, 2011 for EP 10179758.7.

European search report dated Sep. 27, 2010 for EP 10075323.5.

Almeida et al., "Evidence for the involvement of L-arginine-nitric oxide-cyclic guanosine monophosphate pathway in the antidepressant-like effect of memantine in mice" Behavioural Brain Research, vol. 168, No. 2, Apr. 2006, pp. 318-322, XP002445450 ISSN: 0166-4328.

Anand et al., "Dissolution Testing: An FDA Perspective," AAPS Workshop, Physical Pharmacy and Biopharmaceutics, May 13, 2009, 1-32.

Annex A (Letter from Mintz Levin dated Jan. 27, 2009) from Oral Proceedings request of May 30, 2012.

Annex B (Additional data) from Oral Proceedings request of May 30, 2012.

Bakchine and Loft, "Memantine Treatment in Patients with Mild to Moderate Alzheimer's Disease: Results of a Randomised, Double-Blind, Placebo-Controlled 6-Month Study" J Alzheimer's Dis 11: (2007) 471-479.

Bashki et al., "Fatigue in Multiple Sclerosis and Its Relationship to Depression and Neurologic Disability," Mult Scler 6:181-5 (2000).

Bonnet, "Involvement of non-dopaminergic pathways in Parkinson's disease: Pathophysiology and therapeutic implications" CNS Drugs, vol. 13, No. 5, May 2000, pp. 351-364, XP009068859 ISSN: 1172-7047.

Carlton, S.M., Hargett, G.L., Treatment with the NMDA antagonist memantine attenuates nociceptive responses to mechanical stimulation in neuropathic rats. Neurosci. Lett. 198, 115-118. (1995).

Delagarza et al., "Pharmacologic Treatment of Alzheimer's Disease: an Update," Am. Fam. Phys. vol. 68, No. 7, 2003, pp. 136-572.

Dong et al., "Acetylcholinesterase inhibitors ameliorate behavioral deficits in the Tg2576 mouse model of Alzheimer's disease," Psychopharmacology vol. 181, No. 1, 2005, pp. 145-152.

Eisenberg, E., LaCross, S., Strassman, M. The clinically tested N-methyl-D-aspartate receptor antagonist memantine blocks and reverses thermal hyperalgesia in a rat model of painful mononeuropathy. Neurosci. Lett. 187,17-20 (1995).

Engber et al., "NMDA receptor blockade reverses motor response alterations induced by levodopa" Neuroreport, vol. 5, No. 18, 1994, pp. 2586-2588, XP009068863 ISSN: 0959-4965.

EP 05852057 (EP 1827385 A) Third Party Submission Under Art. 115 EPC dated May 25, 2012.

EP 1874282 Patentee's Written Submissions Under Rule 116 EPC dated Sep. 7, 2012.

EP1874282 (Appl. No. 06749777.6) Granted Patent Claims—granted Sep. 15, 2010.

EP1874282 (Appl. No. 06749777.6) Opposition Against Patent dated Jun. 10, 2011.

EP1874282 (Appl. No. 06749777.6) Oral Proceedings Request dated May 30, 2012.

Franz et al., "Percutaneous Absorption on the Relevance of In Vitro Data," J. Invest. Derm. vol. 64, 1975; pp. 194-195.

Fredriksson et al., "Co-administration of memantine and amantadine with sub/suprathreshold doses of L-Dopa restores motor behaviour of MPTP-treated mice" Journal of Neural Transmission, vol. 108, No. 2, 2001, pp. 167-187, XP002389118 ISSN: 0300-9564.

Garcia-Talavera et al., "Atenolol En El Control Del Temblor Parkinsoniano" Medicina Clinica, Doyma, Barcelona, ES, vol. 84, No. 2, Jan. 19, 1985, p. 46, XP001084603 ISSN: 0025-7753.

Greenamyre et al., "Antiparkinsonian effects of remacemide hydrochloride, a glutamate antagonist, in rodent and primate models of Parkinson's disease" Annals of Neurology, vol. 35, No. 6, 1994, pp. 655-661, XP009068858 ISSN: 0364-5134.

Ing et al., "Toxic Effects of Amantadine in Patients with Renal Failure," CMA Journal, Mar. 1979, vol. 120, pp. 695-697.

Johannsen P, "Long-Term Cholinesterase Inhibitor Treatment of Alzheimer's Disease" CNS Drugs (2004) 18(12):757-68.

Jost, "Therapy in the early stage of idiopathic Parkinson's disease" Nervenheilkunde 2005 Germany, vol. 24, No. 1, 2005, pp. 24-28, XP009046893 ISSN: 0722-1541 with English Summary.

Keilhoff et al., Memantine prevents quionlinic acid-induced hippocampal damage. Eur. J. Pharmacol. 219:451-454, (1992).

Koch et al., "Anodic Chemistry of Adamantyl Compounds. Some Scissible Carbon, Halogen, Hydrogen, and Oxygen Substituents" Journal of the American Chemical Society., vol. 95, No. 26, Dec. 26, 1973, pp. 8631-8637, XP002170382 American Chemical Society, Washington, DC., US ISSN: 0002-7863.

Kornhuber and Quack. "Cerebrospinal fluid and serum concentrations of the N-methyl-D-aspartate (NMDA) receptor antagonist memantine in man," *Neurosci. Letters*, 195:137-139 (1995).

Kotani et al., "A New Combined Oxidizing Reagent System, Hexakisacetonitrile Iron(III) periodate: Oxidation of Parrafin Hydrocarbons" Chemical and Pharmaceutical Bulletin, vol. 33, No. 11, Nov. 1985, pp. 4680-4684, XP002170380 Tokyo JP.

Lanctot et al, "Efficacy and safety of cholinesterase inhibitors in Alzheimer's disease: a meta-analysis" Canadian Medical Association Journal (2003) 169:557-64.

Lipton et al., Excitatory Amino Acids as a Final Common Pathway for Neurologic Disorders, N. Engl. J. Med., 330(9) :613-622 (1994).

Maier et al., "Efficacy of the NMDA-receptor antagonist memantine in patients with chronic phantom limb pain—results of a randomized double-blinded, placeo-controlled trial," Pain, 103, pp. 277-283 (2003).

Mann, "The Medical Management of Depression," New England Journal of Medicine, 353 :1819-34 (2005).

Mastrosimone et al.,"Personal Experience With a Combination of Drugs in Subjects With Dopa Resistand Parkinson's Disease" Journal of Medicine, Karger, Basel, CH, vol. 11, No. 5/6, 1980, pp. 377-383, XP009038480 ISSN: 0025-7850.

Mella et al., "Oxidative Functionalization of Adamantane and Some of Its Derivatives in Solution" Journal of Organic Chemistry., vol. 61, No. 4, 1996, pp. 1413-1422, XP002170381 American Chemical Society. Easton., US ISSN: 0022-3263.

Merims D et al., "Riluzole for le vodopa-induced dyskinesias in advanced Parkinson's disease" Lancet the, Lancet Limited. London, GB, vol. 353, No. 9166, May 22, 1999, pp. 1764-1765, XP004826824 ISSN: 0140-6736.

Metman et al., "A Trial of Dextromethorphan in Parkinsonian Patients With Motor Response Complications" Movement Disorders, Raven Press, New York, NY, US, vol. 13, No. 3, May 1998, pp. 414-417, XP009066519 ISSN: 0885-3185.

Metman L Verhagen et al., "Amantadine as treatment for dyskinesias and motor fluctuations in Parkinson's disease" Neurology, vol. 50, No. 5, May 1998, pp. 1323-1326, XP009068857 ISSN: 0028-3878.

Namenda label, NDA 21-487, pp. 1-20. Forest Pharmaceuticals, Inc. (2007).

Neugebauer, V., Kornhuber, J., Lücke, T., Schaible, H.G., The clinically available NMDA receptor antagonist memantine is antinociceptive on rat spinal neurones. Neuroreport 4, 1259-1262. (1993).

Papa et al., "Levodopa-Induced Dyskinesia Improved by a Glutamate Antagonist in Parkinsonian Monkeys" Annals of Neurology, Boston, US, vol. 39, May 1996, pp. 574-578, XP002090027 ISSN: 0364-5134.

Parsons CG, Gruner R, Rozental J, Millar J, Lodge D. Patch clamp studies on the kinetics and selectivity of N-methyl-D-aspartate receptor antagonism by memantine (1-amino-3,5-dimethyladarnantan). *Neuropharmacology* ;32:1337-1350 (1993).

Parsons et al.: 'Glutamate in CNS disorders as a target for drug development: an update', XP002908604 Retrieved from STN Database accession No. 131:13198 & Drug News Perspect. vol. 11, No. 9, 1998, pp. 523-569.

Parsons, et al., 2001) NMDA receptors as targets for drugs in neuropathic pain. Eur. J. Pharmacology, 429, 71-78 (2001).

PCT/US2001/48516 International search report dated Apr. 5, 2002.

PCT/US2005/042780 International Search Report dated Sep. 8, 2006.

PCT/US2005/42424 International search report dated May 8, 2006.

PCT/US2006/013506 International Search Report mailed Jan. 12, 2007.

Pharmaceutical Dosage Forms: Tablets, Second Edition, Revised and Expanded, published by Marcel Dekker, Inc., edited by Lieberman, Lachman, and Schwartz. (1990) pp. 462-472.

"Pharmazeutische Technologie" $5^{th}$ Ed. w/ English Translation (1997).

"Pharmazeutische Technologie" $9^{th}$ Ed. w/ English Translation (2000).

Reichman, "Current pharmacologic options for patients with Alzheimer's disease," Annals of General Hospital Psychiatry, vol. 2, pp. 1-14 (2003).

Remington, The Science and Practice of Pharmacy, $21^{st}$ Ed., pp. 944-945 (2006).

Rogers et al., A 24-week, double-blind, placebo-controlled trial of donepezil in patients with Alzheimer's disease, Neurology (1998) 50:136-45.

Rogoz et al., "Synergistic effect of uncompetitive NMDA receptor antagonists and antidepressant drugs in the forced swimming test in rats" Neuropharmacology, Pergamon Press, Oxford, GB, vol. 42, No. 8, Jun. 2002, pp. 1024-1030, XP002288820 ISSN: 0028-3908.

Shefrin, "Therapeutic advances in idiopathic Parkinsonism" Expert Opinion on Investigational Drugs 1999 United Kingdom, vol. 8, No. 10, 1999, pp. 1565-1588, XP002389119 ISSN: 1354-3784.

Shuto Satoshi et al., "(1S,2R)-1-Phenyl-2-Ä(S)-1-aminopropylÜ-N,N-diethylcyclopropane-carbox amide )PPDC) a New Class of NMDA-Receptor Antagonist: Molecular Design by a Novel Conformational Restriction Strategy" Japanese Journal of Pharmacology, The Japanese Pharmacological Society, Kyoto, JP, vol. 85, No. 3, Mar. 2001, pp. 207-213, XP008021088 ISSN: 0021-5198.

Siegert et al., "Depression in Multiple Sclerosis; a review," J Neurol Neurosurg Psychiatry 76:469-75 (2005).

Snijdelaar et al.,"Effects of Perioperative Oral Amantadine on Postoperative Pain and Morphine Consumption in Patients after Radical Prostatectomy: Results of a Preliminary Study" Anesthesiology 2004 United States, vol. 100, No. 1, Jan. 2004, pp. 134-141, XP009057749 ISSN: 0003-3022.

Sobolevsky AI, Koshelev SG, Khodorov BI. Interaction of memantine and amantadine with agonist-unbound NMDA-receptor channels in acutely isolated rat hippocampal neurons. *J Physiol* (1998) 512(Pt 1):47-60.

Spieker et al.,"The NMDA antagonist budipine can alleviate levodopa-induced motor fluctuations." Movement Disorders : Official Journal of the Movement Disorder Society. May 1999, vol. 14, No. 3, May 1999, pp. 517-519, XP009068946 ISSN: 0885-3185.

Sviridov et al., 'C-hydroxyalkylation of N-adamantylanilines with hexafluoroacetone and methyl trifluoropyruvate', XP002958124 Database Caplus [Online] Retrieved from STN Database accession No. 1990:197720 & IZV. Akad. Nauk SSSR, Ser. Khim. No. 10, 1989, pp. 2348-2350.

Swerdlow et al., "The Effects of Memantine on Prepulse Inhibition," Neuropsychopharmacology, 34, pp. 1854-1864 (2009).

Urbanska et al., "Antiparkinsonian drugs memantine and trihexylphenidyl potentiate the anticonvulsant activity of valproate against maximal electroshock-induced seizures" Neuropharmacology, vol. 31, No. 10, 1992, pp. 1021-1026, XP002332724.

Vale et al., "Amantadine in Depression," Lancet, 11.437 (1971).

Van Dam et al. "Symptomatic effect of donepezil, rivastigmine, galatamine and memantine on cognitive deficits in the APP23 model," Psychopharmacology vol. 180, No. 1, 2005, pp. 177-190.

Weiler et al., "The Use of Propranolol in Alzheimer's Disease Patients With Disruptive Behavior" Current Therapeutic Research, vol. 42, No. 2, Aug. 1987, pp. 364-374, XP001027133.

Wessell et al., "NR2B selective NMDA receptor antagonist CP-101,606 prevents levodopa-induced motor response alterations in hemi-parkinsonian rats" Neuropharmacology, vol. 47, No. 2, Aug. 2004, pp. 184-194, XP002389117 ISSN: 0028-3908.

Wilcock G, Mobius HJ, Stoffler A; MNIM 500 group. A double-blind, placebo-controlled multicentre study of memantine in mild to moderate vascular dementia (MMM500). Int Clin Psychopharmacol. Nov. 2002;17(6):297-305.

Winblad et al., "A 1-year, randomized, placebo-controlled study of donepezil in patients with mild to moderate AD," Neurology (2001) 57 :489-95.

Zarate et al., "A double-blind, placebo-controlled study of memantine in the treatment of major depression" American Journal of Psychiatry, vol. 163, No. 1, Jan. 2006, pp. 153-155, XP009087802 ISSN: 0002-953X.

| Formulation | Time to 20% release (hr) | Time to 80% Release (hr) |
|---|---|---|
| Namenda | 0.044 | 0.19 |
| 5001-6601 | 0.58 | 5.78 |
| 5001-6701 | 3.12 | 9.55 |
| 5001-6801 | 9.16 | 15.10 |
| 5001-6990 | 0.39 | 1.61 |
| 5001-6804 | 13.00 | NA |

| Formulation | Rate of Release (dC/dt at 2 hr) *10e5 | Rate of Release (dC/dt at 4 hr) *10e5 | Cmax | Tmax | (Cmax/Tmax) * 10e5 |
|---|---|---|---|---|---|
| Namenda (10mg) | 353.3 | 569.2 | 0.02389 | 6.2 | 38.53 |
| Namenda (20mg) | 706.5 | 1138 | 0.0119 | 6.2 | 19.26 |
| 5001-6601 | 293.0 | 739.9 | 0.0237 | 17.3 | 13.68 |
| 5001-6701 | 50.1 | 220.5 | 0.0226 | 20.4 | 11.08 |
| 5001-6801 | NA | NA | 0.0232 | 25.1 | 12.17 |
| 5001-6990 | 512 | 1188 | 0.0261 | 7.8 | 33.46 |
| 5001-6804 | NA | NA | 0.0211 | 27.8 | 11.85 |

Bold= lag time was subtracted from the calculation

| Formulation | Time to 20% release (hr) | Time to 80% Release (hr) |
|---|---|---|
| 5001-6990 | 0.39 | 1.61 |
| 5001-6991 | 1.47 | 3.22 |
| 5001-6992 | 3.68 | 7.49 |
| 5001-6993 | 0.79 | 15.6 |
| Namenda | 0.044 | 0.19 |

| Formulation | Time to 20% release (hr) | Time to 80% Release (hr) |
|---|---|---|
| Capsule (13% 5001-6991 & 87% 5001-6992) | 3.18 | 9.36 |

METHOD AND COMPOSITION FOR ADMINISTERING AN NMDA RECEPTOR ANTAGONIST TO A SUBJECT

RELATED APPLICATIONS

This application is a continuation of U.S. application Ser. No. 12/512,701, filed Jul. 30, 2009, now U.S. Pat. No. 8,168,209, which is a division of U.S. application Ser. No. 11/285,905, filed Nov. 22, 2005, now U.S. Pat. No. 7,619,007, issued Nov. 17, 2009, which claims priority to U.S. Provisional Applications 60/630,885, filed Nov. 23, 2004, 60/635,365, filed Dec. 10, 2004, and 60/701,857, filed Jul. 22, 2005, each of which provisional applications is incorporated herein by reference in its entirety; U.S. application Ser. No. 12/512,701 is also a continuation-in-part of U.S. application Ser. No. 11/399,879, filed Apr. 6, 2006, now U.S. Pat. No. 8,058,291, which claims priority to U.S. Provisional Application 60/669,290, filed Apr. 6, 2005, and which is a continuation-in-part of U.S. application Ser. No. 11/285,905, filed Nov. 22, 2005, now U.S. Pat. No. 7,619,007, issued Nov. 17, 2009.

FIELD OF THE INVENTION

The invention relates to compositions containing N-methyl-D-Aspartate receptor (NMDAr) antagonists and methods for using such compositions.

BACKGROUND OF THE INVENTION

Acute and chronic neurological and neuropsychiatric diseases are among the leading causes of death, disability, and economic expense in the world. One of the key challenges in treating these disorders is the high degree of interplay amongst the pathways that control both normal and abnormal neuronal function.

Excitatory amino acid receptors, including the N-Methyl-D-Aspartate (NMDA) receptor, are important mediators of excitatory synaptic transmissions (i.e., stimulation of neurons) in the brain, participating in wide-ranging aspects of both normal and abnormal central nervous system (CNS) function. The NMDA receptor and its associated calcium (Ca2+) permeable ion channel are activated by glutamate, a common excitatory neurotransmitter in the brain and the spinal cord, and the co-agonist glycine. NMDA receptor (NMDAr) activity and consequent Ca2+ influx are necessary for long-term potentiation (a correlate of learning and memory).

Aberrant glutamate receptor activity has been implicated in a large number of CNS-related conditions including, for example, depression and other neuropsychiatric conditions, Parkinson's disease, epilepsy, pain, ALS (amyotrophic lateral sclerosis or Lou Gehrig's disease), and Huntington's disease. In such conditions, the abnormal activation of the NMDA receptor resulting from elevated levels of glutamate may lead to sustained activity of the receptor's ion channel (often lasting for minutes rather than milliseconds), thereby allowing Ca2+ to build-up. This creates both symptomatic and neurodestructive effects on a patient.

Certain NMDAr antagonists, such as memantine and amantadine, readily cross the blood-brain barrier, achieving similar concentrations in the extra cellular fluid surrounding brain tissue and systemic serum. Ideally, NMDAr antagonists should be present at a concentration sufficient to reduce the symptoms or damaging effects of the disease in the absence of debilitating side effects. In the present dosage forms however, these drugs, despite having a relatively long half-lives, need to be administered frequently and require dose escalation at the initiation of therapy to avoid side effects associated with initial exposure to the therapeutic agent. This leads to difficulty in achieving adequate patient compliance, which is further exacerbated by the complicated dosing schedules of therapeutic modalities used for neurological or neuropsychiatric disorders.

Thus, better methods and compositions are needed to treat and delay the progression of neurological disorders.

SUMMARY OF THE INVENTION

In general, the present invention provides pharmaceutical compositions that are administered so as to deliver to a subject, an amount of an NMDAr antagonist that is high enough to treat symptoms or damaging effects of an underlying disease while avoiding undesirable side effects, particularly CNS side effects. These compositions may be employed to administer the NMDAr antagonist at a lower frequency than presently employed (i.e., once a day (q.d.) versus twice a day (b.i.d) or three times a day (t.i.d)), improving patient compliance and caregiver convenience. These compositions are particularly useful as they provide the NMDAr antagonist at a therapeutically effective amount from the onset of therapy further improving patient compliance and adherence and enable the achievement of a therapeutically effective steady-state concentration of the NMDAr antagonist in a shorter period of time. This results in an earlier indication of effectiveness and increasing the utility of these therapeutic agents for diseases and conditions where time is of the essence. Furthermore, the compositions of the present invention, by virtue of their design, allow for higher doses of NMDAr antagonist to be safely administered, again increasing the utility of these agents for a variety of indications. Also provided are methods for making, dosing and using such compositions.

The NMDAr antagonist is desirably provided in a controlled or extended release form, with or without an immediate release component in order to maximize the therapeutic benefit of the NMDAr antagonist, while reducing unwanted side effects. In the absence of modified release components (referred to herein as controlled, extended or delayed release components), the NMDAr antagonist is released and transported into the body fluids over a period of minutes to several hours. In a preferred embodiment, the composition of the invention contains an NMDAr antagonist and a sustained release component, such as a coated sustained release matrix, a sustained release matrix, or a sustained release bead matrix. In one example, memantine (e.g., 5-80 mg) is formulated without an immediate release component using a polymer matrix (e.g., Eudragit), Hydroxypropyl methyl cellulose (HPMC) and a polymer coating (e.g., Eudragit). Such formulations are compressed into solid tablets or granules and coated with a controlled release material such as Opadry® or Surelease®.

NMDAr Antagonists.

The NMDAr antagonist may be an aminoadamantine derivative such as memantine (1-amino-3,5-dimethyladamantane), rimantadine (1-(1-aminoethyl)adamantane), or amantadine (1-amino-adamantane) as well as others described below.

Excipients

The excipients used to produce the formulation may include bulking agents, lubricants, glidants, and release controlling agents. Many such materials are found in "Remington: The Science and Practice of Pharmacy, Twentieth Edition," Lippincott Williams & Wilkins, Philadelphia, Pa. and commonly known to the skilled artisan. The specific excipients used will be determined by the requirements for administration of the dosage, including the targeted dosing frequency, slope of drug release and absorption, and route of administration. In one embodiment, the formulation does not contain a casein salt.

Dosage Form

The NMDAr antagonist may be formulated as a suspension, capsule, tablet, suppository, lotion, patch, or device (e.g., a subdermally implantable delivery device or an inhalation pump). In preferred embodiments, the dosage form is provided for oral administration, e.g. as a capsule.

Release Profile

The compositions described herein are formulated such the NMDAr antagonist has an in vitro dissolution profile that is slower than that for an immediate release (IR) formulation. As used herein, the immediate release (IR) formulation for memantine means the present commercially available 5 mg and 10 mg tablets (i.e., Namenda from Forest Laboratories, Inc. or formulations having substantially the same release profiles as Namenda); and for the immediate release (IR) formulation of amantadine means the present commercially available 100 mg tablets (i.e., Symmetrel from Endo Pharmaceuticals, Inc. or formulations having substantially the same release profiles as Symmetrel). These compositions may contain immediate release, sustained or extended release, delayed release components, or combinations thereof. Thus, the present compositions may be formulated such that the fraction of the NMDAr antagonist released is greater or equal to $0.01(0.297+0.0153*e^{(0.515*t)})$ and less than $1-e^{(-10.9*t)}$, as measured using a USP type 2 (paddle) dissolution system at 50 rpm, at a temperature of 37±0.5° C., in water, where t is the time in hours and t is greater than zero and equal or less than 17. Thus, the fraction of NMDAr antagonist that is released is less than 93% in 15 minutes and 7.7%100% in 12 hours using a USP type 2 (paddle) dissolution system at 50 rpm, at a temperature of 37±0.5° C. in a neutral pH (e.g. water or buffered aqueous solution) or acidic (e.g. 0.1 N HCl) dissolution medium. Optionally, the fraction of released NMDAr antagonist is greater or equal to $0.01(0.297+0.0153*e^{(0.515*t)})$ and less than or equal to $1-e^{(-0.972*t)}$ as measured using a USP type 2 (paddle) dissolution system at 50 rpm, at a temperature of 37±0.5° C., in water, where t is the time in hours and t is greater than zero and equal or less than 17. Optionally, the fraction of released NMDAr antagonist is greater or equal to $0.01(-2.75+2.75*e^{(0.21*t)})$ and less than or equal to $1-e^{(-0.40*t)}$ as measured using a USP type 2 (paddle) dissolution system at 50 rpm, at a temperature of 37±0.5° C., in water, where t is the time in hours and t is greater than zero and equal or less than 17. Thus, the fraction of NMDAr antagonist that is released may range between 0.1%-62% in one hour, 0.2%-86% in two hours, 0.6%-100% in six hours, 2.9%-100% in 10 hours, and 7.7%-100% in 12 hours using a USP type 2 (paddle) dissolution system at 50 rpm, at a temperature of 37±0.5° C. in a neutral pH (e.g. water or buffered aqueous solution) or acidic (e.g. 0.1 N HCl) dissolution medium. Optionally, the fraction of NMDAr antagonist that is released may range between 0.6%-33% in one hour, 1.4%-55% in two hours, 6.9%-91% in six hours, 19.7%-98% in 10 hours, and 31%-100% in 12 hours using a USP type 2 (paddle) dissolution system at 50 rpm, at a temperature of 37±0.5° C. in a neutral pH (e.g. water or buffered aqueous solution) or acidic (e.g. 0.1 N HCl) dissolution medium. Optionally, the NMDA receptor antagonist has a release profile ranging between 0.1%-20% in one hour, 5%-30% in two hours, 40%-80% in six hours, 70% or greater (e.g., 70%-90%) in 10 hours, and 90% or greater (e.g., 90-95%) in 12 hours as measured in a dissolution media having a neutral pH (e.g. water or buffered aqueous solution) or in an acidic (e.g. 0.1 N HCl) dissolution medium. For example, a formulation containing memantine may have a release profile ranging between 0-60% or 0.1-20% in one hour, 0-86% or 5-30% at two hours, 0.6-100% or 40-80% at six hours, 3-100% or 50% or more (e.g., 50-90%) at ten hours, and 7.7-100% at twelve hours in a dissolution media having a neutral pH (e.g. water or buffered aqueous solution) or in an acidic (e.g. 0.1 N HCl) dissolution medium.

In one embodiment, the NMDAr antagonist has an in vitro dissolution profile of less than 25%, 15%, 10%, or 5% in fifteen minutes; 50%, 30%, 25%, 20%, 15%, or 10% in 30 minutes and more than 60%, 65% 70%, 75%, 80%, 85%, 90%, 95% at 16 hours as obtained using a USP type II (paddle) dissolution system at 50 rpm, at a temperature of 37±0.5° C. in water. Desirably, the NMDAr antagonist has a dissolution of at least 65%, 70%, 75%, 80%, 85%, 90%, or 95% in a dissolution media having a pH of 1.2 at 10 hours.

Desirably, the compositions described herein have an in vitro profile that is substantially identical to the dissolution profile shown in FIGS. 2A-2C and, upon administration to a subject at a substantially constant daily dose, achieves a serum concentration profile that is substantially identical to that shown in FIG. 2D.

Initial Rate of Release In Vivo

As used herein, "C" refers to the concentration of an active pharmaceutical ingredient in a biological sample, such as a patient sample (e.g. blood, serum, and cerebrospinal fluid). The concentration of the drug in the biological sample may be determined by any standard assay method known in the art. The term "Cmax" refers to the maximum concentration reached by a given dose of drug in a biological sample. The term "Cmean" refers to the average concentration of the drug in the sample over time. Cmax and Cmean may be further defined to refer to specific time periods relative to administration of the drug. The time required to reach the maximal concentration ("Cmax") in a particular patient sample type is referred to as the "Tmax". The change in concentration is termed "dC" and the change over a prescribed time is "dC/dT".

Desirably, the NMDAr antagonist is released into a subject sample at a slower rate than observed for an immediate release (IR) formulation of the same quantity of the antagonist, such that the rate of change in the biological sample measured as the dC/dT over a defined period within the period of 0 to Tmax for the IR formulation and the dC/dT rate is less than about 80%, 70%, 60%, 50%, 40%, 30%, 20%, or 10% of the rate for the IR formulation (e.g., Namenda, a commercially available IR formulation of memantine). In some embodiments, the dC/dT rate is less than about 80%, 70%, 60%, 50%, 40%, 30%, 20%, or 10% of the rate for the IR formulation. Similarly, the rate of release of the NMDAr antagonist from the present invention as measured in dissolution studies is less than 80%, 70%, 60% 50%, 40%, 30%, 20%, or 10% of the rate for an IR formulation of the same NMDAr antagonist over the first 1, 2, 4, 6, 8, 10, or 12 hours.

In a preferred embodiment, the dosage form is provided in a non-dose escalating, twice per day or once per day form. In such cases, the concentration ramp (or Tmax effect) may be reduced so that the change in concentration as a function of time (dC/dT) is altered to reduce or eliminate the need to dose escalate the drug. A reduction in dC/dT may be accomplished, for example, by increasing the Tmax in a relatively proportional manner. Accordingly, a two-fold increase in the Tmax value may reduce dC/dT by approximately a factor of 2. Thus, the NMDAr antagonist may be provided so that it is released at a rate that is significantly reduced over an immediate release (so called IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5 or at least 0.8. In certain embodiments, this is accomplished by releasing less than 30%, 50%, 75%, 90%, or 95% of the NMDAr antagonist into the circulatory or neural system within one hour of such administration.

Optionally, the modified release formulations exhibit plasma concentration curves having initial (e.g., from 2 hours after administration to 4 hours after administration) slopes less than 75%, 50%, 40%, 30%, 20% or 10% of those for an IR formulation of the same dosage of the same NMDAr antagonist. The precise slope for a given individual will vary according to the NMDAr antagonist being used, the quantity delivered, or other factors, including, for some active pharmaceutical agents, whether the patient has eaten or not. For other doses, e.g., those mentioned above, the slopes vary directly in relationship to dose.

Using the sustained release formulations or administration methods described herein, the NMDAr antagonist reaches a therapeutically effective steady state plasma concentration in a subject within the course of the first three, five, seven, nine, ten, twelve, fifteen, or twenty days of administration. For example, the formulations described herein, when administered at a substantially constant daily dose (e.g., at a dose ranging between 15 mg and 80 mg, preferably between 20 mg and 65 mg, and more preferably between 20 mg and 45 mg per day) may reach a steady state plasma concentration in approximately 70%, 60%, 50%, 40%, 30%, or less of the time required to reach such plasma concentration when using a dose escalating regimen.

Reduced Cmax, Extented Tmax

In a preferred embodiment of this invention, at least 75%, 90%, 95%, 97%, 98%, 99% or even 100% of the NMDAr antagonist is provided in a modified or extended release dosage form and upon the administration of this composition to a subject (e.g., a mammal such as a human), the NMDAr antagonist has a Cmax/C mean of approximately 2.5, 2, 1.5, or 1.0, approximately 1, 1.5, 2 hours to at least 6, 9, 12, 18, 21, 24 hours following such administration. If desired, the release of the NMDAr antagonist may be monophasic or multiphasic (e.g., biphasic). Desirably, 99%, 98%, 95%, 90%, 85%, 80%, 70%, 50%, or 30% of the NMDAr antagonist remains in an extended release dosage form within one hour of such administration.

Dosing Frequency Reduction

The compositions and methods of the instant invention also enable a reduction in the dosing frequency. For example, an NMDAr antagonist ordinarily administered two to four times per day when dosing in an IR form may be provided to the subject once or twice per day using the formulations described herein. In some embodiments, the compositions described herein are administered even less frequently, e.g. every 2 days, every 3 days, every week, or every month.

Non-Dose Escalation

Immediate release (IR) formulations of NMDAr antagonists are typically administered in a dose-escalating fashion, frequently starting with subtherapeutic amounts of the agent. Although dosing adjustments or individualization may be managed by a physician for a pharmaceutical composition the compositions described herein may be administered at an essentially constant, therapeutically-effective dose from the initiation of therapy, thereby improving patient and caregiver compliance, adherence, and convenience.

Furthermore, the compositions described herein enable the use of higher doses of NMDAr antagonist equal or fewer adverse effects than observed for IR formulations of the same agent, increasing the utility of the NMDAr antagonist for indications described herein.

Reduced Time to Therapeutic Concentration and Efficacy

The administration of the compositions described herein at therapeutically effective doses from the initiation of therapy enables the attainment of a steady state level of the agent in a shorter time period (e.g. 20%, 30%, 50%, 70%, 90% less time than for dose-escalated regimens), thus enabling the treatment of more acute disorders such as pain and neuropsychiatric disorders, including depression, agitation, bipolar disorder, and drug dependency, withdrawal, or tolerance.

Conditions Amenable to Treatment

The compositions of the present invention may be employed to treat or reduce the symptoms associated with deregulation in NMDA receptor activity or conditions that would benefit from a reduction in such activity. Further, many NMDAr antagonists have other known activities (e.g. the dopaminergic activity of amantadine, the antiviral activity of rimantadine). The compositions of the present invention are also useful to treat, prevent, or reduce conditions associated with such activities in any subject having or at risk of having a such condition. Exemplary conditions include seizure disorders, pain syndromes, neurodegenerative diseases (including motor neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillian-Barre syndrome, dysproteinemias, transthyretin-induced neuropathies, and carpal tunnel syndrome).

Alternate Routes of Administration

In one embodiment, the compositions described herein are formulated as tablets or capsules for oral administration or patches for transdermal delivery of the NMDAr antagonist. Alternatively, the compositions may be prepared in other ways for these routes of administration (e.g. as a suspension for oral administration) or specifically for other administrative routes intravenous, topical, intranasal, subtopical transepithelial, subdermal, or inhalation delivery.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting. All parts and percentages are by weight unless otherwise specified.

Figure 1A:
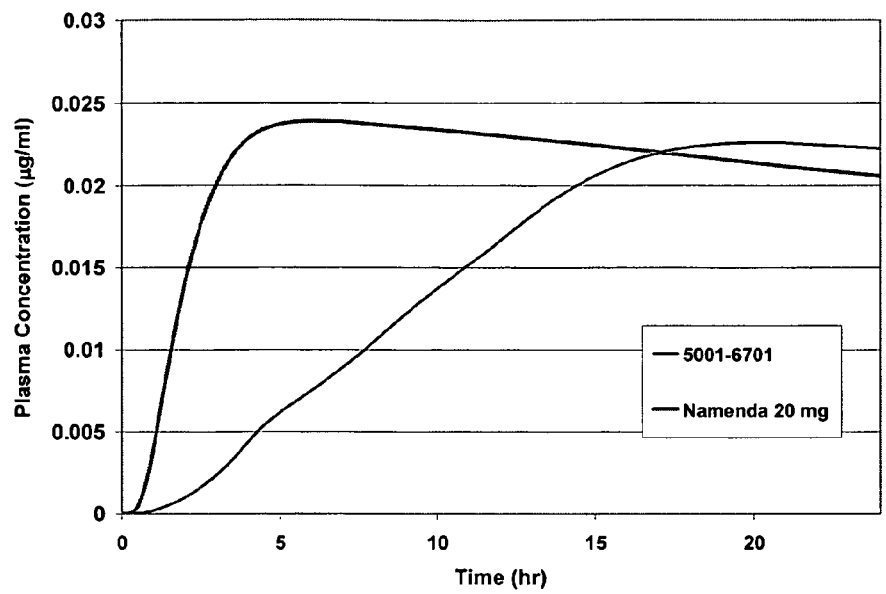
FIG. 1A is a graph showing the memantine plasma concentration over a period of 24 hours, as predicted by Gastro-Plus software package v.4.0.2, following the administration of a single dose of an immediate release (IR) formulation of memantine (Namenda) or a sustained release formulation of memantine (NPI-6701). The sustained release formulation exhibits a dC/dT during the initial phase that is about 20% of that for the immediate release (IR) formulation.
Figure 1B:
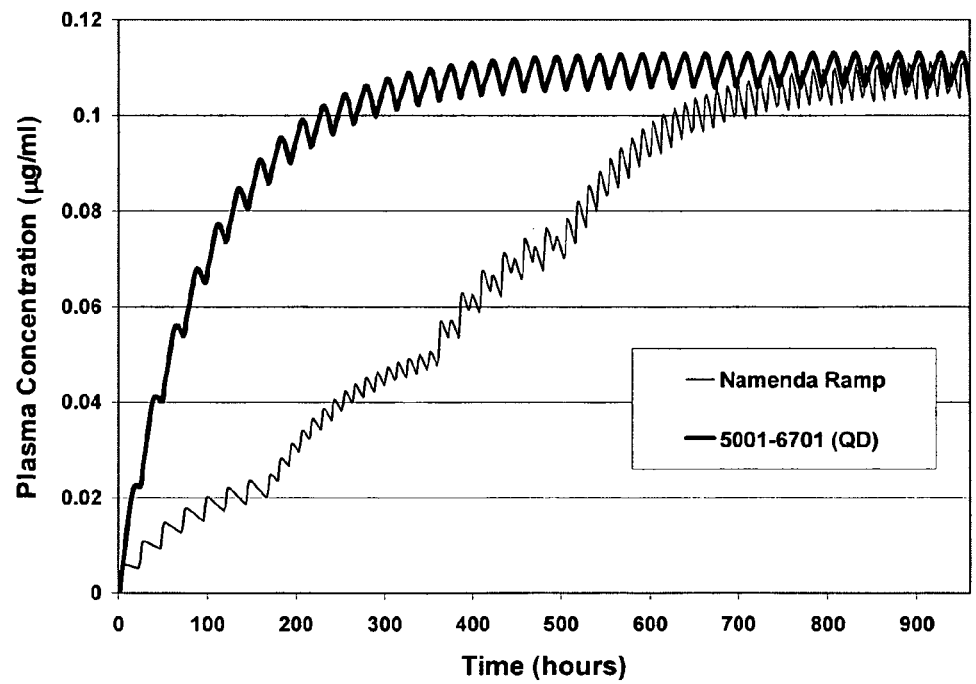
FIG. 1B is a graph showing the memantine plasma concentration over a period of 28 days, as predicted by Gastro-Plus software package v.4.0.2, following the administration of an immediate release (IR) formulation of memantine (Namenda) and a sustained release formulation of memantine (NPI-6701). When Namenda is administered using a dose escalation regimen pursuant to the manufacturer's US FDA approved label, a steady-state therapeutically effective plasma concentration is reached within about 30 days. The administration of a sustained release formulation of memantine at a constant dose (e.g., 22.5 mg/day) achieves a steady therapeutically effective plasma concentration within about 13 days, a reduction of about 60%.

Other features and advantages of the invention will be apparent from the following detailed description and claims.

DETAILED DESCRIPTION OF THE INVENTION

In general, the present invention features pharmaceutical compositions that contain an NMDAr antagonist formulated for extended or modified release to provide a serum or plasma concentration over a desired time period that is high enough to be therapeutically effective but at a rate low enough so as to avoid adverse events associated with the NMDAr antagonist. Control of drug release is particularly desirable for reducing and delaying the peak plasma level while maintaining the extent of drug bioavailability. Therapeutic levels are therefore achieved while minimizing debilitating side-effects that are usually associated with immediate release formulations. Furthermore, as a result of the delay in the time to obtain peak serum or plasma level and the extended period of time at the therapeutically effective serum or plasma level, the dosage frequency is reduced to, for example, once or twice daily dosage, thereby improving patient compliance and adherence. For example, side effects including psychosis and cognitive deficits associated with the administration of NMDAr antagonists may be lessened in severity and frequency through the use of controlled-release methods that shift the Tmax to longer times, thereby reducing the dC/dT of the drug. Reducing the dC/dT of the drug not only increases Tmax, but also reduces the drug concentration at Tmax and reduces the Cmax/Cmean ratio providing a more constant amount of drug to the subject being treated over a given period of time enabling a increased dosages for appropriate indications.

Making NMDAr Antagonist Controlled Release Formulations

A pharmaceutical composition according to the invention is prepared by combining a desired NMDAr antagonist or antagonists with one or more additional ingredients that, when administered to a subject, causes the NMDAr antagonist to be released at a targeted rate for a specified period of time. A release profile, i.e., the extent of release of the NMDAr antagonist over a desired time, can be conveniently determined for a given time by measuring the release using a USP dissolution apparatus under controlled conditions. Preferred release profiles are those which slow the rate of uptake of the NMDAr antagonist in the neural fluids while providing therapeutically effective levels of the NMDAr antagonist. One of ordinary skill in the art can prepare combinations with a desired release profile using the NMDAr antagonists and formulation methods described below.

NMDAr Antagonists

Any NMDAr antagonist can be used in the methods and compositions of the invention, particularly those that are non-toxic when used in the compositions of the invention. The term "nontoxic" is used in a relative sense and is intended to designate any substance that has been approved by the United States Food and Drug Administration ("FDA") for administration to humans or, in keeping with established regulatory criteria and practice, is susceptible to approval by the FDA or similar regulatory agency for any country for administration to humans or animals.

The term "NMDAr antagonist", as used herein, includes any amino-adamantane compound including, for example, memantine (1-amino-3,5-dimethyladamantane), rimantadine (1-(1-aminoethyl)adamantane), amantadine (1-aminoadamantane), as well as pharmaceutically acceptable salts thereof. Memantine is described, for example, in U.S. Pat. Nos. 3,391,142, 5,891,885, 5,919,826, and 6,187,338. Amantadine is described, for example, in U.S. Pat. Nos. 3,152,180, 5,891,885, 5,919,826, and 6,187,338. Additional aminoadamantane compounds are described, for example, in U.S. Pat. Nos. 4,346,112, 5,061,703, 5,334,618, 6,444,702, 6,620,845, and 6,662,845. All of these patents are hereby incorporated by reference.

Further NMDAr antagonists that may be employed include, for example, amino cyclohexanes (i.e., neramexane), ketamine, eliprodil, ifenprodil, dizocilpine, remacemide, iamotrigine, riluzole, aptiganel, phencyclidine, flupirtine, celfotel, felbamate, spermine, spermidine, levemopamil, dextromethorphan ((+)-3-hydroxy-N-methylmorphinan) and its metabolite, dextrorphan ((+)-3-hydroxy-N-methylmorphinan), a pharmaceutically acceptable salt, derivatives or ester thereof, or a metabolic precursor of any of the foregoing.

Optionally, the NMDAr antagonist in the instant invention is memantine and not amantadine or dextromethorphan.

Dosing, PK, & Tox

The pharmaceutical composition may be formulated to provide memantine in an amount ranging between 1-200 mg/day, 1 and 80 mg/day, 2-80 mg/day, 5-80 mg/day, 5 and 65 mg/day, 5 and 40 mg/day, 15 and 45 mg/day, or 10 and 20 mg/day; amantadine in an amount ranging between 15 and 900 mg/day, 15 mg and 800 mg/day, 15 mg and 700 mg/day, 15 mg and 600 mg/day, 15 and 500 mg/day, 25 and 500 mg/day, 15 and 400 mg/day, 25 and 300 mg/day, 100 and 300 mg/day, or 100 and 200 mg/day; dextromethorphan in an amount ranging between 1-5000 mg/day, 1-1000 mg/day, and 100-800 mg/day, or 200-500 mg/day. Pediatric doses will typically be lower than those determined for adults.

Table 1 shows exemplary the pharmacokinetic properties (e.g., Tmax and T1/2) of memantine, amantadine, and rimantadine.

TABLE 1

Pharmacokinetics and Tox in humans for selected NMDAr antagonists

| Compound | Human PK (t½) (hours) | Tmax (hours) | Normal Dose | Dose Dependent Tox |
|---|---|---|---|---|
| Memantine | 60 | 3 | 10-20 mg/day, starting at 5 mg | Dose escalation required, hallucination |
| Amantadine | 15 | 3 | 100-300 mg/day, starting at 100 mg/day | Hallucination |
| Rimantadine | 25 | 6 | 100-200 mg/day | Insomnia |

Excipients

"Pharmaceutically or Pharmacologically Acceptable" includes molecular entities and compositions that do not produce an adverse, allergic or other untoward reaction when administered to an animal, or a human, as appropriate. "Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The preparation of pharmaceutical or pharmacological compositions are known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragées, gels, slurries, ointments, solutions suppositories, injections, inhalants and aerosols are examples of such formulations.

By way of example, extended or modified release oral formulation can be prepared using additional methods known in the art. For example, a suitable extended release form of the either active pharmaceutical ingredient or both may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The NMDAr antagonist may be formulated using any of the following excipients or combinations thereof.

| Excipient name | Chemical name | Function |
|---|---|---|
| Avicel PH 102 | Microcrystalline Cellulose | Filler, binder, wicking, disintegrant |
| Avicel PH 101 | Microcrystalline Cellulose | Filler, binder, disintegrant |
| Eudragit RS-30D | Polymethacrylate Poly(ethyl acrylate, nethyl methacrylate, timethylammonioethyl methacrylate chloride) 1:2:0.1 | Film former, tablet binder, tablet diluent; Rate controlling polymer for controlled release |
| Methocel K100M Premium CR | Hydroxypropyl methylcellulose | Rate controlling polymer for controlled release; binder; viscosity-increasing agent |

-continued

| Excipient name | Chemical name | Function |
|---|---|---|
| Methocel K100M | Hydroxypropyl methylcellulose | Rate controlling polymer for controlled release; binder; viscosity-increasing agent |
| Magnesium Stearate | Magnesium Stearate | Lubricant |
| Talc | Talc | Dissolution control; anti-adherent, glidant |
| Triethyl Citrate | Triethyl Citrate | Plasticizer |
| Methocel E5 | Hydroxypropyl methylcellulose | Film-former |
| Opadry ® | Hydroxypropyl methylcellulose | One-step customized coating system which combines polymer, plasticizer and, if desired, pigment in a dry concentrate. |
| Surelease ® | Aqueous Ethylcellulose Dispersion | Film-forming polymer; plasticizer and stabilizers. Rate controlling polymer coating. |

The pharmaceutical composition described herein may also include a carrier such as a solvent, dispersion media, coatings, antibacterial and antifungal agents, isotonic and absorption delaying agents. The use of such media and agents for pharmaceutically active substances is well known in the art. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, may also be used as a carrier.

Methods for Preparing Modified or Extended Release Formulations

Suitable methods for preparing the compositions described herein in which the NMDAr antagonist is provided in extended release-formulations include those described in U.S. Pat. No. 4,606,909 (hereby incorporated by reference). This reference describes a controlled release multiple unit formulation in which a multiplicity of individually coated or microencapsulated units are made available upon disintegration of the formulation (e.g., pill or tablet) in the stomach of the subject (see, for example, column 3, line 26 through column 5, line 10 and column 6, line 29 through column 9, line 16). Each of these individually coated or microencapsulated units contains cross-sectionally substantially homogenous cores containing particles of a sparingly soluble active substance, the cores being coated with a coating that is substantially resistant to gastric conditions but which is erodable under the conditions prevailing in the gastrointestinal tract.

The composition of the invention may alternatively be formulated using the methods disclosed in U.S. Pat. No. 4,769,027, for example. Accordingly, extended release formulations involve prills of pharmaceutically acceptable material (e.g., sugar/starch, salts, and waxes) may be coated with a water permeable polymeric matrix containing an NMDAr antagonist and next overcoated with a water-permeable film containing dispersed within it a water soluble particulate pore forming material.

The NMDAr antagonist composition may additionally be prepared as described in U.S. Pat. No. 4,897,268, involving a biocompatible, biodegradable microcapsule delivery system. Thus, the NMDAr antagonist may be formulated as a composition containing a blend of free-flowing spherical particles obtained by individually microencapsulating quantities of memantine, for example, in different copolymer excipients which biodegrade at different rates, therefore releasing memantine into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D,L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

Alternatively, the composition may be prepared as described in U.S. Pat. No. 5,395,626, which features a multilayered controlled release pharmaceutical dosage form. The dosage form contains a plurality of coated particles wherein each has multiple layers about a core containing an NMDAr antagonist whereby the drug containing core and at least one other layer of drug active is overcoated with a controlled release barrier layer therefore providing at least two controlled releasing layers of a water soluble drug from the multilayered coated particle.

Release Profile (Dissolution Rate)

As described above, the NMDAr antagonist may be provided in a modified or extended release form. Extended or modified drug release is generally controlled either by diffusion through a coating or matrix or by erosion of a coating or matrix by a process dependent on, for example, enzymes or pH. The NMDAr antagonist may be formulated for extended or modified release as described herein or using standard techniques in the art. In one example, at least 50%, 75%, 90%, 95%, 96%, 97%, 98%, 99%, or even in excess of 99% of the NMDAr antagonist is provided in an extended release dosage form.

Figure 2A:
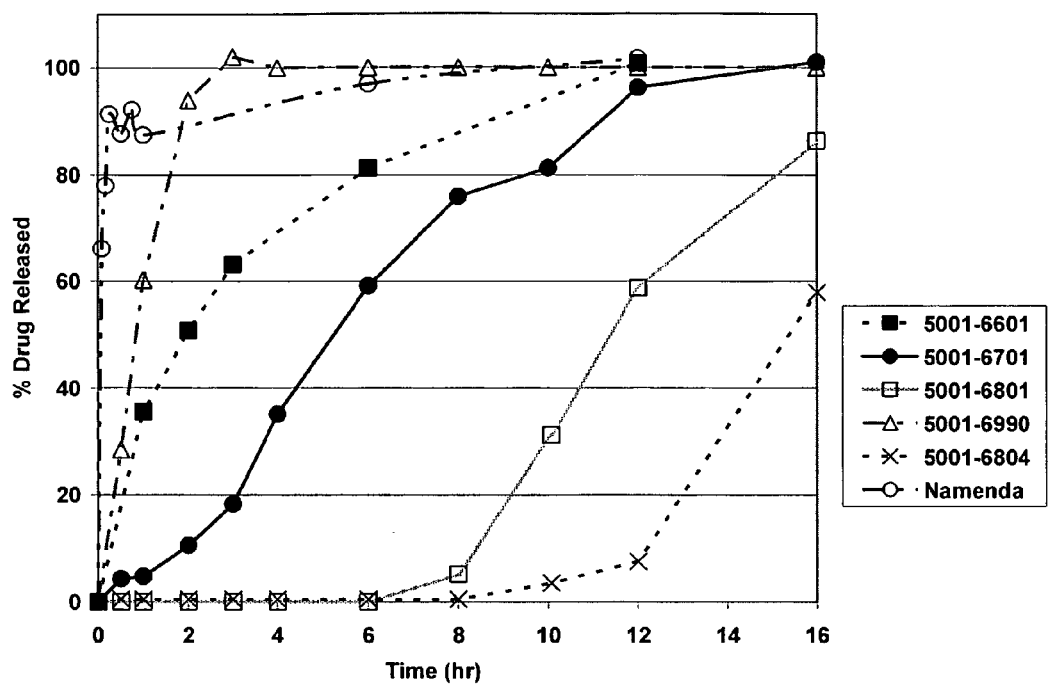
FIG. 2A is a graph and a table showing the in vitro dissolution profiles for various sustained release formulations of memantine (NPI-6601, NPI-6701, NPI-6801, NPI-6990, and NPI-6804) and Namenda. Dissolution profiles were obtained with a USP II (Paddle) system using water as a dissolution medium.
Figure 2B:
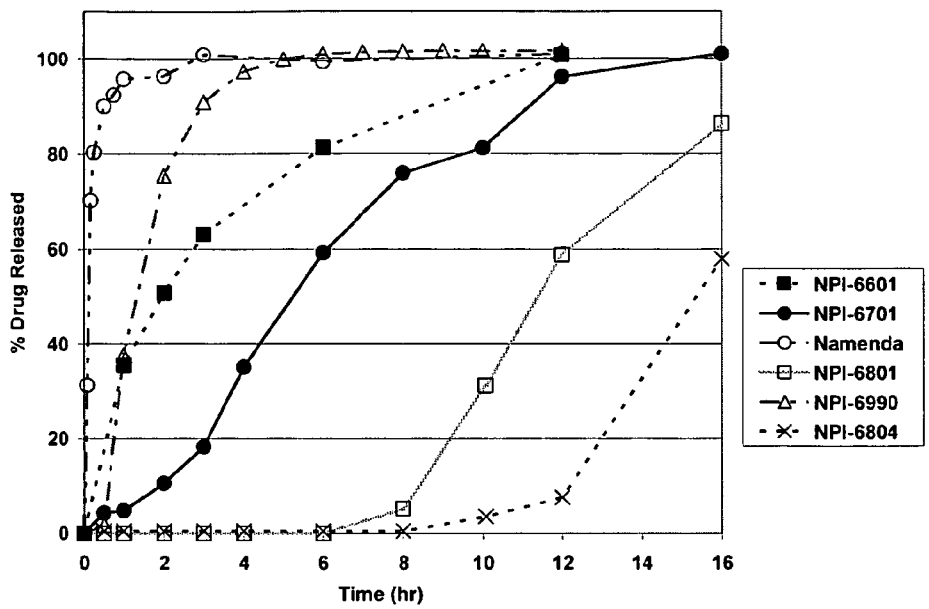
FIG. 2B is a graph showing the dissolution profiles for various sustained release formulations of memantine (NPI-6601, NPI-6701, NPI-6801, NPI-6990, and NPI-6804) and Namenda obtained with a USP II (Paddle) system using 0.1N hydrochloride solution pH=1.2 as the dissolution medium.
Figure 2C:
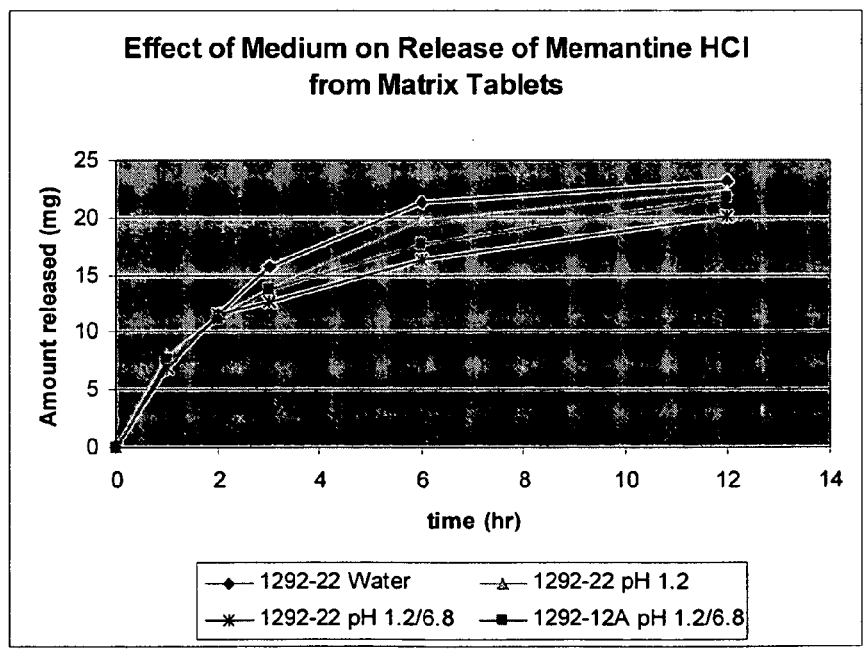
FIG. 2C is a graph showing the dissolution profile of memantine formulated as a sustained release form using a neutral (e.g., water) and acidic (pH 1.2) dissolution medium.
Figure 2D:
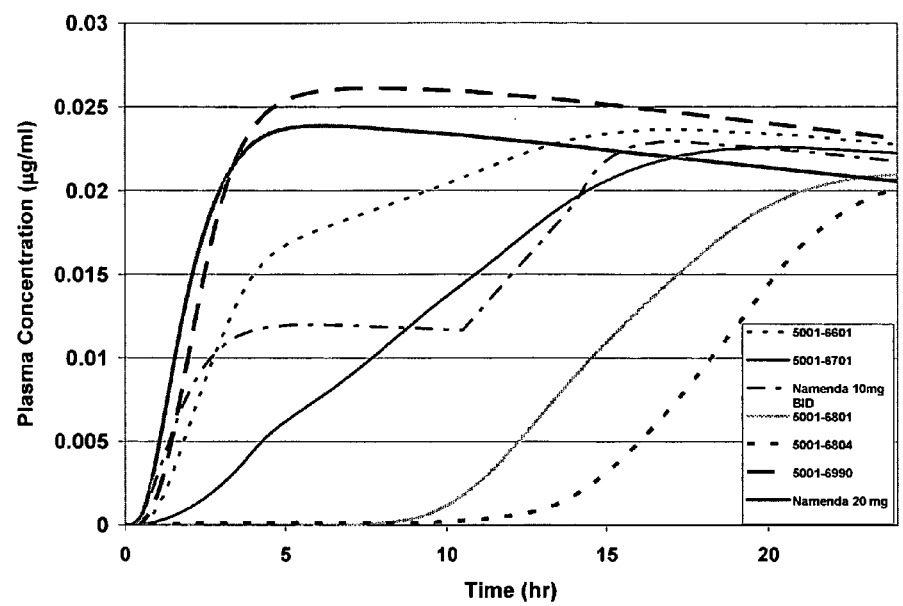
FIG. 2D is a graph and table showing the memantine plasma concentration over a period of 24 hours, as predicted by Gastro-Plus software package v.4.0.2, following the administration of Namenda (10 mg b.i.d. or single dose of 20 mg) or various sustained release formulations of memantine (i.e., NPI-6601, NPI-6701, NPI-6801, NPI-6804, and NPI-6990 administered at a single dose of 22.5 mg).
Figure 3A:
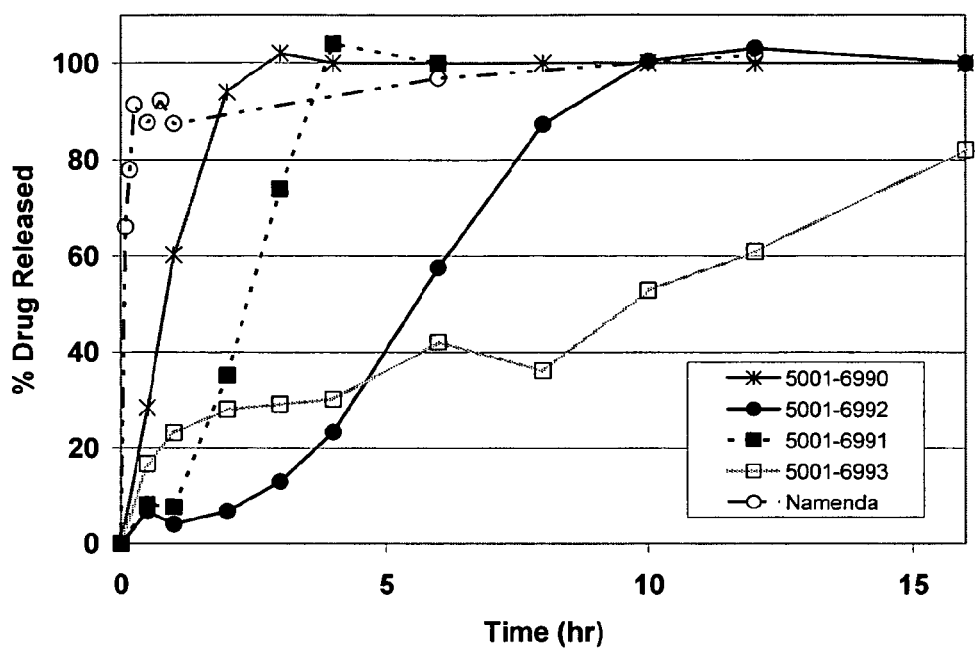
FIG. 3A is a graph and table showing the dissolution profiles for various sustained released memantine bead/capsule formulations. The experimental dissolution profiles were obtained from a USP II Paddle system using water (pH=7) as the medium.
Figure 3B:
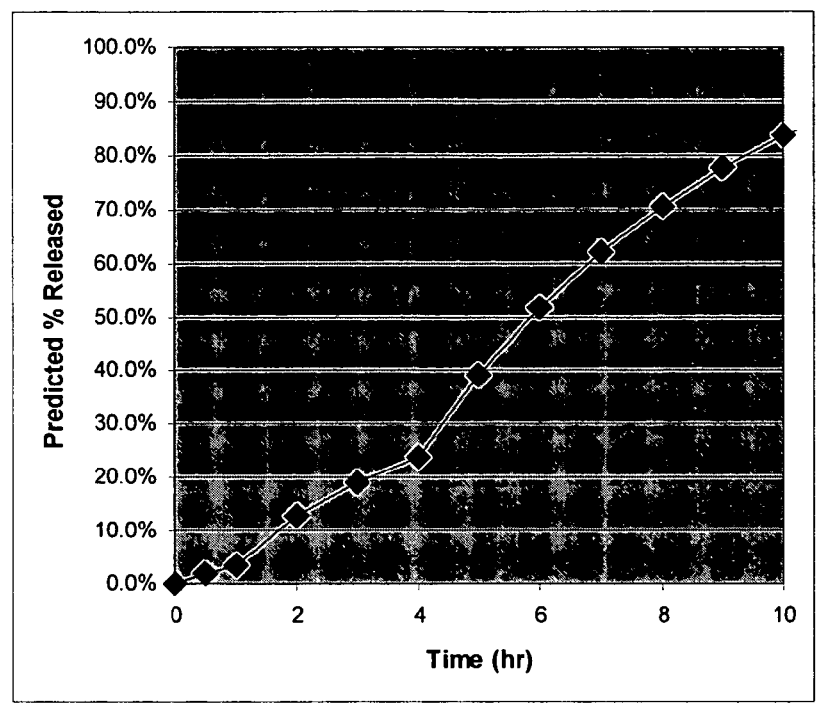
FIG. 3B is a graph and table showing the predicted dissolution profile for a simple two-bead composite capsule (13% of 5001-6991 & 87% of 5001-6992).
Figure 4:
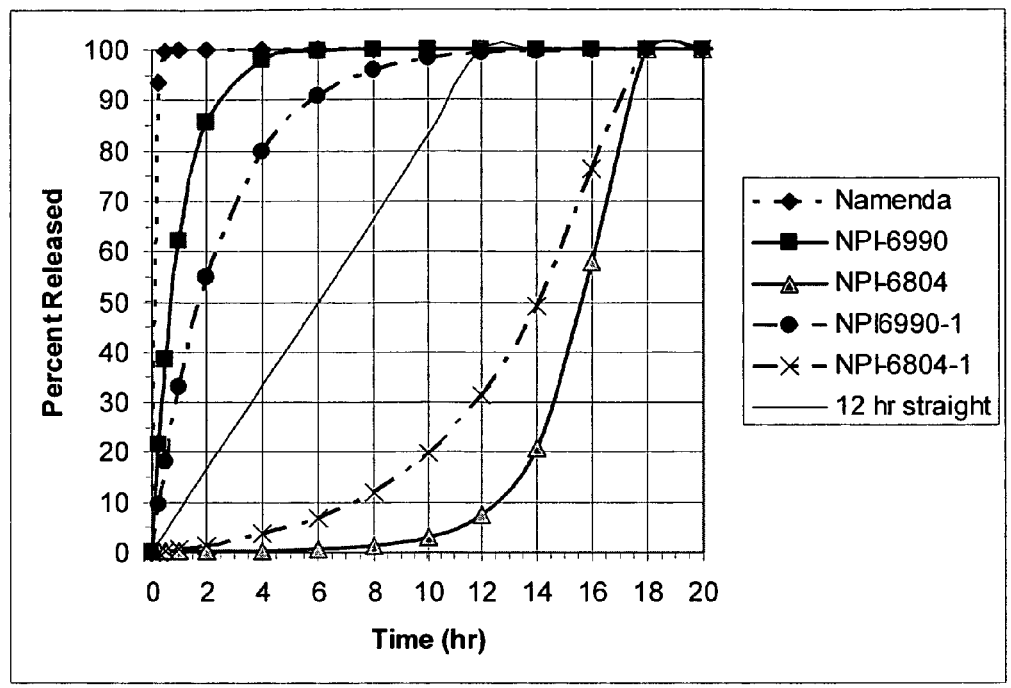
FIG. 4 is a graph showing dissolution profiles for modified release formulations of memantine and an IR formulation of memantine (Namenda).

Optionally, the compositions described herein have an in vitro profile that is substantially identical to the dissolution profile shown in FIGS. 2A-2C and, upon administration to a subject at a substantially constant daily dose, achieves a serum concentration profile that is substantially identical to that shown in FIG. 2D. The dissolution profile of the composition of the invention may be determined using a USP type 2 (paddle) dissolution system at 50 rpm, at a temperature of 37±0.5° C. in various dissolution media. In one example, the release fraction is greater or equal to $0.01(0.297+0.0153*e^{(0.515*t)})$ and less than $1-e^{(-10.9*t)}$. In another example, the release fraction is greater or equal to $0.01(0.297+0.0153*e^{(0515*t)})$ and less than or equal to $1-e^{(-0.972*t)}$. In both examples, the term "t" is the time in hours and t is greater than zero and equal or less than 17. Thus, the NMDAr antagonist may have an in vitro dissolution profile that ranges between 0.1%-62% in one hour, 0.2%-86% in two hours, 0.6%-100% in six hours, 2.9%-100% in 10 hours, and 7.7%-100% in 12 hours using a USP type 2 (paddle) dissolution. Optionally, the release profile may range between 0.1%-20% in one hour, 5%-30% in two hours, 40%-80% in six hours, 50%-90% in 10 hours, and 90%-95% in 12 hours. Desirably, the NMDAr antagonist has an in vitro dissolution profile in a solution with a neutral pH (e.g., water) that is substantially the same as its dissolution profile in an acidic dissolution medium (see FIGS. 2A-2C).

In one embodiment, the NMDAr antagonist has an in vitro dissolution profile of less than 15%, 10%, or 5% in fifteen minutes, 25%, 20%, 15%, or 10% in 30 minutes, and more than 60% at 16 hours as obtained using a USP type II (paddle) dissolution system at 50 rpm, at a temperature of 37±0.5° C. in water. Desirably, the NMDAr antagonist has a dissolution of at least 65%, 70%, 75%, 80%, 85%, 90%, or 95% at 10 hours in a dissolution medium having a pH of 1.2.

Initial Rate In Vivo, Delayed Tmax, Reduced Cmax/Cmean

The NMDAr antagonist is provided as a modified release formulation that may or may not contain an immediate release formulation. If desired, the NMDAr antagonist may formulated so that it is released at a rate that is significantly reduced over an immediate release (IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5 or at least 0.8. In addition, the NMDAr antagonist may be provided such that it is released at rate resulting in a Cmax/C mean of approximately 2 or less for approximately 2 hours to at least 8 hours after the NMDAr antagonist is introduced into a subject. Optionally, the sustained release formulations exhibit plasma concentration curves having initial (e.g., from 0, 1, 2 hours after administration to 4, 6, 8 hours after administration) slopes less than 75%, 50%, 40%, 30%, 20% or 10% of those for an IR formulation of the same dosage of the same NMDAr antagonist. The precise slope for a given individual will vary according to the NMDAr antagonist being used or other factors, including whether the patient has eaten or not. For other doses, e.g., those mentioned above, the slopes vary directly in relationship to dose. The determination of initial slopes of plasma concentration is described, for example, by U.S. Pat. No. 6,913,768, hereby incorporated by reference.

Thus, upon the administration to a subject (e.g., a mammal such as a human), the NMDAr antagonist has a Cmax/Cmean of approximately 2.5, 2, 1.5, or 1.0 approximately 1, 1.5, 2 hours to at least 6, 8, 9, 12, 18, 21, 24 hours following such administration. If desired, the release of the NMDAr antagonist may be monophasic or multiphasic (e.g., biphasic). One of ordinary skill in the art can prepare compositions with a desired release profile using the NMDAr antagonists and formulation methods known in the art or described below.

Dosing Frequency and Dose Escalation

According to the present invention, a subject (e.g., human) having or at risk of having such conditions is administered any of the compositions described herein (e.g., once a day, every 2 days, every 3 days, every week, or every month). While immediate formulations of NMDAr antagonists are typically administered in a dose-escalating fashion, the compositions described herein may be essentially administered at a constant, therapeutically-effective dose over a set period of time. For example, a composition containing a sustained release formulation of memantine may be administered twice a day, once a day, once every two days, or once every three days in a unit dose containing 10-300 mg, 10-200 mg, 10-100 mg, or 10-50 mg of memantine (e.g., 10 mg, 11.25 mg, 12.5 mg, 15 mg, 20 mg, 22.5 mg, 25 mg, 30 mg, 33.75 mg, 37.5 mg, 40 mg, 45 mg, 50 mg, 60 mg, 65 mg, 67.5 mg, 70 mg, 75 mg, 80 mg, 120 mg, 180 mg, 240 mg or 300 mg).

In one embodiment, a composition is prepared using the methods described herein, wherein such composition comprises memantine or amantadine and a release modifying excipient. The excipient is present in an amount sufficient to ameliorate or reduce acute toxicity associated with the memantine or amantadine relative to an immediate release (IR) formulation of memantine (e.g., Namenda) or amantadine (e.g., Symmetrel). The use of such composition increases the safety in the administration of such agents, enabling reduced dosing frequency with similar or higher doses of the NMDAr antagonist as compared with the presently available forms of these pharmaceutical products.

Reduced Time to Therapeutic Concentration and Efficacy

Immediate release (IR) formulations of memantine (e.g., Namenda) are typically administered at low doses (e.g., 5 mg/day) and progressively administered at increasing frequency and dose over time to reach a steady state serum concentration that is therapeutically effective. According to the manufacturer's FDA approved label, Namenda, an immediate release (IR) formulation of memantine, is first administered to subjects at a dose of 5 mg per day. After a period of time one week acclimation period, subjects are administered with this dose twice daily. Subjects are next administered with a 5 mg and 10 mg dosing per day and finally administered with 10 mg Namenda twice daily. FIG. 2D shows the average serum concentration each day as predicted by the pharmacokinetic software, GastroPlus, from Simulations Plus. Using this dosing regimen, a therapeutically effective steady state serum concentration may be achieved within 30 days of the onset of therapy. Using a modified release formulation comprising (22.5 mg memantine,) however, a therapeutically effective steady state concentration may be achieved substantially sooner, without using a dose escalating regimen. As shown in FIG. 2D, such concentration is predicted to be achieved within thirteen days of the onset of therapy. Furthermore, the slope during each absorption period for the sustained release formulation is less (i.e. not as steep) as the slope for Namenda. Accordingly, the dC/dT of the sustained release formulation is reduced relative to the immediate release formulation even though the dose administered is larger than for the immediate release formulation. Based on this model, a sustained release formulation of memantine may be administered to a subject in an amount that is approximately the full strength dose (or that effectively reaches a therapeutically effective dose) from the onset of therapy and throughout the duration of treatment. Accordingly, a dose escalation would not be required.

Thus in one embodiment, a composition is prepared using the methods described herein, wherein such composition comprises a therapeutically effective amount of memantine or amantadine and an excipient for administration to a subject without prior administration of a subtherapeutic amount of same active agent (i.e. memantine or amantadine) to the same subject. Specifically, for an indication such as Alzheimer's disease, where a therapeutically effective amount of memantine is typically 20 mg per day, the administration of memantine to the subject is initiated at 22.5 mg per day or more, instead of a subtherapeutic amount (e.g., 5 mg per day as currently indicated in the manufacturer's FDA-approved label for Namenda).

Treatment of a subject with the subject of the present invention may be monitored using methods known in the art. The efficacy of treatment using the composition is preferably evaluated by examining the subject's symptoms in a quantitative way, e.g., by noting a decrease in the frequency or severity of symptoms or damaging effects of the condition, or an increase in the time for sustained worsening of symptoms. In a successful treatment, the subject's status will have improved (i.e., frequency or severity of symptoms or damaging effects will have decreased, or the time to sustained progression will have increased). In the model described in the previous paragraph, the steady state (and effective) concentration of the NMDAr antagonist is reached in 25% 40% 50% 60% 70% 75% 80% less time than the dose escalated approach.

In another embodiment, a composition is prepared using the methods described herein, wherein such composition comprises memantine or amantadine and a release modifying excipient, wherein the excipient is present in an amount sufficient to ameliorate or reduce the dose-dependent toxicity associated with the memantine or amantadine relative to an immediate release (IR) formulation of memantine, such as Namenda, or amantadine, such as Symmetrel. The use of these compositions enables safer administration of these agents, and even permits the safe use of higher levels for appropriate indications, beyond the useful range for the presently available versions of memantine (5 mg and 10 mg per dose to 20 mg per day) and amantadine (100 mg to 300 mg per day with escalation).

Indications Suitable for Treatment

Conditions suitable for treatment according to this invention include seizure disorders, pain syndromes, neurodegenerative diseases (including motor neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillian-Barre syndrome, dysproteinemias, transthyretin-induced neuropathies, and carpal tunnel syndrome).

As used herein, seizure disorders include complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, mesial temporal lobe epilepsy, nocturnal frontal lobe epilepsy, progressive epilepsy with mental retardation, and progressive myoclonic epilepsy, as well as seizures associated with CNS mass lesions.

Pain syndromes include, for example, headaches (e.g., migraine, tension, and cluster), acute pain, chronic pain, neuropathic pain, nociceptive pain, central pain and inflammatory pain, drug-induced neuropathic pain, causalgia, complex regional pain syndrome types I and II, and reflex sympathetic dystrophy (RSDS).

Neurodegenerative diseases include Alzheimer's disease, Parkinson's Disease, multiple sclerosis, Huntington's Disease, ALS, spinal muscular atrophy, muscular dystrophies prion-related diseases, cerebellar ataxia, Friedrich's ataxia, SCA, Wilson's disease, RP, Gullian Barre syndrome, Adrenoleukodystrophy, Menke's Sx, cerebral autosomal dominant arteriopathy with subcortical infarcts (CADASIL), Charcot Marie Tooth diseases, neurofibromatosis, von-Hippel Lindau, Fragile X, spastic paraplegia, tuberous sclerosis complex, Wardenburg syndrome, spinal motor atrophies, Tay-Sach's, Sandoff disease, familial spastic paraplegia, myelopathies, radiculopathies, encephalopathies associated with trauma, radiation, drugs and infection, and disorders of the sympathetic nervous system (e.g., Shy Drager (familial dysautonomia), diabetic neuropathy, drug-induced and alcoholic neuropathy).

Dementias include Alzheimer's disease, Parkinson's disease, Pick's disease, fronto-temporal dementia, vascular dementia, normal pressure hydrocephalus, Huntington's disease, and MCI.

Cerebrovascular conditions amenable to treatment according to the present invention include Cerebrovascular disease and strokes (e.g, thrombotic, embolic, thromboembolic, hemorrhagic (including AVM and berry aneurysms), venoconstrictive, and venous).

Included in movement disorders are Parkinson's disease, dystonias, benign essential tremor, tardive dystonia, tardive dyskinesia, and Tourette's syndrome.

Brain trauma as used herein includes traumatic brain and spinal cord injuries as well as brain injuries from radiation.

Cranial nerve disorders include trigeminal neuropathy, trigeminal neuralgia, Menier's syndrome, glossopharangela neuralgia, dysphagia, dysphonia, cranial nerve palsies and Bell's palsy.

Neuropsychiatric disorders include panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence/additiction (e.g., alcohol, psychostimulants (eg, crack, cocaine, speed, meth), opioids, and nicotine), and drug-induced psychiatric disorders.

Other disease neuropathies that may be treated with the compositions and methods described herein include Guillian-Barre, diabetes associated neuropathies, dysproteinemias, transthyretin-induced neuropathies, neuropathy associated with HIV, herpes viruses (including herpes zoster) or other viral infection, neuropathy associated with Lyme disease, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, post-menengitis syndrome, post-polio syndrome, prion diseases, and radiation associated neuropathic syndromes.

Other diseases amenable to treatment with the present invention include fatigue syndromes (e.g., chronic fatigue syndrome and fibromyalgia), ataxic syndromes, olivopontoicerebellar degeneration, striatonigral degeneration, and axonic brain damage.

Because the NMDAr antagonist in the present compositions reaches a therapeutically effective steady state in a shorter period of time than immediate release formulations (e.g., within the course of the first five, seven, nine, ten, twelve, fifteen, or twenty days of administration), the present invention is particularly useful for the treatment of neuropsychiatric disorders such as depression, agitation, anxiety, seizure disorders such as grand mal seizures, status epilepticus, migraine pain treatment and prophylaxis, Alzheimer's disease, Parkinson's disease, and traumatic brain and spinal cord injury.

Also, the higher doses enabled by the present invention are expected to be of particular importance for dementias including Alzheimer's disease, Parkinson's disease, and vascular dementia, pain syndromes, including headaches and migraines, seizure disorders, movement disorders, and brain trauma.

Furthermore, the ease of use and convenience of a dosage form provided developed to be delivered at once per day or less frequent administration at a therapeutically effective quantity from the onset of therapy is of value in treatment of dementias including Alzheimer's disease and Parkinson's disease, seizure disorders, pain syndromes, and cerebrovascular conditions.

Formulations for Alternate Specific Routes of Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The NMDAr antagonist may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

In some embodiments, for example, the composition may be delivered intranasally to the cribriform plate rather than by inhalation to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs.

Additional formulations suitable for other modes of administration include rectal capsules or suppositories. For suppositories, traditional binders and carriers may include, for example, polyalkylene glycols or triglycerides; such suppositories may be formed from mixtures containing the active ingredient in the range of 0.5% to 10%, preferably 1%-2%.

The composition may optionally be formulated for delivery in a vessel that provides for continuous long-term delivery, e.g., for delivery up to 30 days, 60 days, 90 days, 180 days, or one year. For example the vessel can be provided in a biocompatible material such as titanium. Long-term delivery formulations are particularly useful in subjects with chronic conditions, for assuring improved patient compliance, and for enhancing the stability of the compositions.

Optionally, the NMDA receptor antagonist is prepared using the OROS® technology, described for example, in U.S. Pat. Nos. 6,919,373, 6,923,800, 6,929,803, 6,939,556, and 6,930,128, all of which are hereby incorporated by reference. This technology employs osmosis to provide precise, controlled drug delivery for up to 24 hours and can be used with a range of compounds, including poorly soluble or highly soluble drugs. OROS® technology can be used to deliver high drug doses meeting high drug loading requirements. By targeting specific areas of the gastrointestinal tract, OROS® technology may provide more efficient drug absorption and enhanced bioavailability. The osmotic driving force of OROS® and protection of the drug until the time of release eliminate the variability of drug absorption and metabolism often caused by gastric pH and motility.

Formulations for continuous long-term delivery are provided in, e.g., U.S. Pat. Nos. 6,797,283; 6,764,697; 6,635,268, and 6,648,083.

If desired, the components may be provided in a kit. The kit can additionally include instructions for using the kit.

Additional Methods for Making Modified Release Formulations

Additional methods for making modified release formulations are described in, e.g., U.S. Pat. Nos. 5,422,123, 5,601,845, 5,912,013, and 6,194,000, all of which are hereby incorporated by reference.

Alternatively, the compositions of the present invention may be administered transdermally. Preparation for delivery in a transdermal patch can be performed using methods also known in the art, including those described generally in, e.g., U.S. Pat. Nos. 5,186,938 and 6,183,770, 4,861,800, 6,743,211, 6,945,952, 4,284,444, and WO 89/09051, incorporated herein by reference in their entireties. A patch is a particularly useful embodiment with drugs having absorption problems. Patches can be made to control the release of skin-permeable active ingredients over a 12 hour, 24 hour, 3 day, and 7 day period. In one example, a 2-fold daily excess of an NMDAr antagonist is placed in a non-volatile fluid. Given the amount of the agents employed herein, a preferred release will be from 12 to 72 hours.

Transdermal preparations of this form will contain from 1% to 50% active ingredients. The compositions of the invention are provided in the form of a viscous, non-volatile liquid. Preferably, the NMDAr antagonist will have a skin penetration rate of at least 10-9 mole/cm2/hour. At least 5% of the active material will flux through the skin within a 24 hour period. The penetration through skin of specific formulations may be measures by standard methods in the art (for example, Franz et al., J. Invest. Derm. 64:194-195 (1975)). Providing the NMDAr antagonist in the form of patches is useful given that these agents have relatively high skin fluxes.

In some embodiments, for example, the composition may be delivered via intranasal, buccal, or sublingual routes to the brain rather than by inhalation to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs.

Preparation of a pharmaceutical composition for delivery in a subdermally implantable device can be performed using methods known in the art, such as those described in, e.g., U.S. Pat. Nos. 3,992,518; 5,660,848; and 5,756,115.

Using the formulations and methods described herein, we have produced numerous formulations of NMDAr antagonists (e.g., memantine and amantadine) having modified release profiles (more than 50). Exemplary formulations are provided in the Examples.

The invention will be illustrated in the following non-limiting examples.

EXAMPLES

Example 1

Measuring Release Profiles for Aminoadamantanes In Vitro

Compositions containing an aminoadamantane were analyzed for release of the aminoadamantane, according to the USP type II apparatus at a speed of 50 rpm. The dissolution media used were water, 0.1N HCl, or 0.1N HCl adjusted to pH 6.8 at 2 hours with phosphate buffer. The dissolution medium was equilibrated to 37±0.5° C.

The USP reference assay method for amantadine was used to measure the fraction of memantine released from the compositions prepared herein. Briefly, 0.6 mL sample (from the dissolution apparatus at a given time point) was placed into a 15 mL culture tube. 1.6 mL 0.1% Bromocresol Purple (in acetic acid) was added and vortexed for five seconds. The mixture was allowed to stand for approximately five minutes. 3 mL Chloroform was added and vortexed for five seconds. The solution was next centrifuged (speed 50 rpm) for five minutes. The top layer was removed with a disposable pipette. A sample was drawn into 1 cm flow cell and the absorbance was measured at 408 nm at 37° C. and compared against a standard curve prepared with known quantities of the same aminoadamantane. The quantity of determined was plotted against the dissolution time for the sample.

Example 2

Preparation of Memantine-Containing Cores to be Coated with an Enteric Coating

Memantine-containing cores are prepared as follows and as described, for example, in U.S. Pat. No. 4,606,909. Cores (containing 24% talc) are prepared using 0.97 kg memantine, 0.2 kg sodium laurylsulphate, 0.5 kg microcrystalline cellulose, 5.93 kg saccharose powder, and 2.4 kg talc. Memantine and sodium laurylsulphate are co-comminuted by passage through a grinder using a 0.5 mm sieve. The ground mixture is mixed with microcrystalline cellulose, saccharose, and talc in a planet mixer. 10 kg of the resulting mixture is moistened with 0.8 kg purified water and mixed in a planet mixer until the mixture is slightly lumpy. The moist mixture is extruded through a 0.5 mm sieve. The first kilograms of extrudate passing the sieve is powdery and re-extruded. The resulting extrudates form strings, breaking off in lengths of 10-30 cm. 2 kg of the extruded strings is formed into compact-shaped cores in a Marumerizer™ and the resulting compact-shaped cores are dried in a fluidized bed dryer and sieved through a separator (the upper sieve (0.71 mm) and the bottom sieve (0.46 mm). Using the same technique, cores (containing 10% talc) are prepared using 0.97 kg memantine, 0.2 kg sodium laurylsulphate, 1.0 kg microcrystalline cellulose, 6.83 kg saccharose powder, and 1.0 kg talc.

The release of memantine is measured, at a pH 7.5 for the cores containing 24% talc and 10% talc, respectively. The reduction in the talc content from 24% to 10% decreases the release weight of memantine from the core.

An enteric coating suspension, which further delays the release of memantine, is prepared by homogenizing 9.0 kg Eudragit™ S 12.5 together with 0.135 kg acetyltributylcitrate, 0.9 kg talc, and 7.965 kg isopropanol. 10 kg of the above-described cores containing 10% talc are coated with 4.167 kg of this coating suspension in a fluidized bed and the resulting pellets are covered with talcum. For the preparation of a pharmaceutical dosage form, 1000 of these pellets are filled in a capsule No. 1, such that each of the capsule contains 25 mg memantine.

Example 3

Preparation of Amantadine Extended Release Capsules

Amantadine extended release capsules may be formulated as follows or as described, for example, in U.S. Pat. No. 5,395,626.

A. Composition: Unit Dose

The theoretical quantitative composition (per unit dose) for amantadine extended release capsules is provided below.

| Component | % weight/weight | mg/Capsule |
| --- | --- | --- |
| Amantadine | 68.34 | 200.00 |
| OPADRY ® Clear YS-3-7011 [1] | 1.14 | 5.01 |
| (Colorcon, Westpoint, PA) | | |
| Purified Water, USP [2] | — | — |
| Sugar Spheres, NF | 12.50 | 54.87 |
| OPADRY ® Clear YS-1-7006 [3] | 4.48 | 19.66 |
| (Colorcon, Westpoint, PA) | | |
| SURELEASE ® E-7-7050 [4] | 13.54 | 59.44 |
| (Colorcon, Westpoint, PA) | | |
| Capsules [5] | — | — |
| TOTAL | 100.00% | 338.98 mg [6] |

[1] A mixture of hydroxypropyl methylcellulose, polyethylene glycol, propylene glycol.
[2] Purified Water, USP is evaporated during processing.
[3] A mixture of hydroxypropyl methylcellulose and polyethylene glycol
[4] Solid content only of a 25% aqueous dispersion of a mixture of ethyl cellulose, dibutyl sebacate, oleic acid, ammoniated water and fumed silica. The water in the dispersion is evaporated during processing.
[5] White, opaque, hard gelatin capsule, size 00.
[6] Each batch is assayed prior to filling and the capsule weight is adjusted as required to attain 200 mg amantadine per capsule.

The quantitative batch composition for amantadine extended release capsule is shown below. (Theoretical batch quantity 25,741 capsules):

| Step 1: Prep of Amantadine HCl Beads (bead Build-up #1) | |
| --- | --- |
| Component | Weight (kg) |
| Amantadine | 12.000 |
| OPADRY ® Clear YS-3-7011 | 0.200 |
| Purified Water, USP | 5.454 |
| Sugar Sphere, NF | 4.000 |
| Total Weight Amantadine Beads | 16.200 kg |

The amantadine beads obtained from step 1 are used as follows.

| Step 2: Clear & Sustained Release Bead Coating #1 | |
| --- | --- |
| Component | Weight (kg) |
| Amantadine Beads | 8.000 |
| OPADRY ® Clear YS-1-7006 | 0.360 |
| Purified Water, USP | 5.928 |
| Surelease ® E-7-7050 | 0.672 |
| Total Weight Clear Coated Sustained Release Beads | 9.032 kg |

The sustained release beads obtained from step 2 are used as follows.

| Step 3: Amantadine HCl Beads (Build-up #2) | |
|---|---|
| Component | Weight (kg) |
| Sustained Release Beads | 8.000 |
| Amantadine | 4.320 |
| OPADRY ® Clear YS-3-7011 | 0.072 |
| Purified Water, USP | 1.964 |
| Total Weight Amantadine Beads | 12.392 kg |

The amantadine beads obtained from step 3 are formulated as follows.

| Step 4: Clear & Sustained Release Bead Coating #2 | |
|---|---|
| Component | Weight (kg) |
| Amantadine Beads | 10.000 |
| OPADRY ® Clear YS-1-7006 | 0.250 |
| Purified Water, USP | 6.450 |
| Surelease ® E-7-7050 | 1.050 |
| Total Weight Amantadine Extended Release Beads | 11.300 kg |

Step 5: Capsule Filling—Gelatin capsules, size 00, are filled with 339 mg of the amantadine beads prepared in step 4.

Examples 4-11

Extended release formulation of Rimantidine

The NMDAr antagonist, rimantidine, is formulated for extended release as follows (see, for example, U.S. Pat. No. 5,912,013).

Example 4

Core Pellets

| | Weight Percent | Kilograms |
|---|---|---|
| MCC | 25.0 | 0.25 |
| Hydroxypropylmethylcellulose Phthalate (HPMCP) | 10.0 | 0.10 |
| Tartaric Acid | 10.0 | 0.10 |
| Sodium Monoglycerate | 7.5 | 0.075 |
| DSS | 0.5 | 0.005 |
| Rimantadine | 47.0 | 0.47 |
| TOTAL | 100.0% | 1.00 kg |
| Coating | | |
| Cellulose Acetate Phthalate (CAP) | 60.0 | 0.60 |
| Ethylcellulose | 25.0 | 0.25 |
| PEG-400 | 15.0 | 0.15 |
| TOTAL | 100.0% | 1.00 kg |

Example 5

Coating for Core Pellets from Example 4

| | Weight Percent | Kilograms |
|---|---|---|
| Ethacrylic/Methacrylic Acid Esters (Eudragit line of enteric polymers) | 85.0 | 0.85 |
| Propylene Glycol | 14.0 | 0.14 |
| Talc | 1.0 | 0.01 |
| TOTAL | 100.0% | 1.00 kg |

Example 6

Coating for Core Pellets from Example 4

| | Weight Percent | Kilograms |
|---|---|---|
| CAP | 65.0 | 0.65 |
| HPMCP | 15.0 | 0.15 |
| PEG-400 | 10.0 | 0.10 |
| PEG-8000 | 10.0 | 0.10 |
| TOTAL | 100.0% | 1.00 kg |

Example 7

Core Pellet

| Coating as in Example 4 | | |
|---|---|---|
| | Weight Percent | Kilograms |
| MCC | 25.0 | 0.25 |
| Mono/Di/Tri-glyceride Mixture | 15.0 | 0.15 |
| Tartaric Acid | 10.0 | 0.10 |
| CAP | 10.0 | 0.10 |
| DSS | 0.8 | 0.008 |
| Rimantadine | 39.2 | 0.392 |
| TOTAL | 100.0% | 1.00 kg |

Example 8

Core Pellet as in Example 8, Coating as in Example 5

Example 9

Core Pellet as in Example 8, Coating as in Example 6

Example 10

Coating for Core Pellet as in Example 9

|  | Weight Percent | Kilograms |
|---|---|---|
| Shellac | 85.0 | 0.85 |
| Mineral Oil | 13.0 | 0.13 |
| SLS | 0.5 | 0.005 |
| Talc | 1.5 | 0.015 |
| TOTAL | 100.0% | 1.00 kg |

Example 11

Core Pellet as in Example 4, Coating as in Example 10

Example 12

Preparation of Memantine Controlled Release

Different sustained release tablet formulations of memantine were developed, each of which is associated with a characteristic in vitro dissolution profile. As described in further detail below, the sustained release formulations reach a superior pharmacokinetic profile therapeutically. The sustained release profile was achieved using a sustained release matrix or a sustained release coated tablet. The physical characteristics of the active, a description of the formulation composition, an outline of the small scale production process, and the validated analytical methods are presented below.

Drug Substance Information

| API Name | Memantine |
|---|---|
| Molecular Weight | 215.8 for HCl salt, 178.3 for free base |
| Melting Point ° C. | 258-295° C. |
| $pK_a$ | 10.27 |
| Aqueous Solubility | 40-45 mg/ml at pH 2-9 |
| Stability | $T_{1/2}$ > 24 hours in aqueous buffer, pH 4.0-7.4 and rat plasma |

Formulation Composition

Formulation #1: Memantine formulated with a sustained release matrix

| Type of Tablet | Formulation #1 Sustained release matrix | Formulation #2 Sustained release coated tablet |
|---|---|---|
| Memantine HCL (22.5 mg) | 13.5% | 15.25% |
| Avicel PH102 | 60.0% | 69.0% |
| Eudragit RS-30D (aqueous dispersion) | 15.4% | 14.8% |
| HPMC K100M | 10.1% | — |
| Magnesium Stearate | 1.0% | 1.0% |
| Coating: | — | Additional 6% coat |
| 70% Eudragit RL-30D (aqueous dispersion) |  | 21% |
| 30% Eudragit RS-30D (aqueous dispersion) |  | 9% |
| Talc |  | 9% |
| TEC |  | 2% |
| $H_2O$ |  | 59% |
| Total Tablet Weight | 150 mg | 159 mg |

Formulation #1 was produced as follows. Memantine was formulated as shown in the table below.

| Component Core Tablets - 22.5 mg - Formulation 1292-22.5-10A | % Comp. Solid weight | mg/tablet Solid weight | Total weight (g) |
|---|---|---|---|
| Granulation from 1292-12-150 grams | | | |
| Memantine HCl | 13.51 | 22.5 | 22.79 |
| Avicel ® PH102 | 60.04 | 100.0 | 101.28 |
| Eudragit RS-30D (30% w/v aqueous dispersion) | 15.37 | 25.6 | 25.92 |
| Extragranular Excipient | | | |
| HPMC K100M | 10.08 | 16.8 | 17.00 |
| Magnesium Stearate | 1.01 | 1.6 | 1.7 |
| Total | 100.0 | 166.5 | 168.7 (solid weight) |

API is bag blended with Avicel PH102 and sieved through an 18-mesh screen. The mix is next dried in a low shear mixer. The blend is wet massed with Eudragit and the granulation is dried in an oven at 40-45° C. for 12 hours. The granulation is next pass dried through an Alexanderwerk Mill set up with 0.8 mm screen, producing the intermediate active blend. HPMC was sieved through a 30 mesh screen. The screened HPMC was premixed with an equal amount of the intermediate active blend, referred to herein as 1292-12 and bag blended for two minutes. The blend was next lubricated with Magnesium Stearate in a low shear blender. A sample from this blend was collected for LOD (Loss on Drying) testing on Computrac MAx 2000 set at 105° C. The final blend is then compressed and tables are punched using a D3B set up with 0.25 inch standard round concave punch tooling. The dissolution profile of this formulation is provided in FIG. 6 (% Label claim vs. time).

Formulation 2: Memantine Formulated Using A Sustained Release Coated Matrix

| Component Core Tablets - 22.5 mg - | % Comp. Solid weight | mg/tablet Solid weight | Total weight (g) |
|---|---|---|---|
| Memantine HCl active | 15.25 | 22.5 | 93.80 |
| Avicel ® PH102 | 68.96 | 101.75 | 424.20 |

| Component<br>Core Tablets - 22.5 mg - | % Comp.<br>Solid<br>weight | mg/tablet<br>Solid<br>weight | Total<br>weight (g) |
|---|---|---|---|
| Eudragit RS-30D (30% w/v aqueous dispersion) | 14.79 | 21.83 | 303.3* |
| Extragranular Excipient | | | |
| HPMC K100M | 10.08 | 16.8 | 17.00 |
| Magnesium Stearate | 1.01 | 1.6 | 1.7 |
| Total | 100.0 | 166.5 | 168.7 (solid weight) |

*303.3 g of Eudragit RS-30D aqueous dispersion contains 91 g of solid polymer and 212.3 g of liquid.

Memantine HCl is first bag blended with Avicel PH102 for one minute. The dry blend is sieved through an 18 mesh screen into a poly bag and bag blended for one minute. The mixture is loaded into a low-shear mixer and dried for two minutes. The blend was wet massed with Eudragit and the granulation was next dried in an oven at 40-45° C. for 12 hours. The dried granulation is next passed through an Alexanderwerk Mill set up with a 0.8 mm screen. Sieved magnesium stearate (30-mesh) was next added to the milled mix and bag blended. The final blend was next compressed and tablets were punched using a D3B 0.25 inch standard round punch.

The coat tablet was prepared as follows. To prepare the coat, Eudragit RL-30D & Eudragit RS-30D was added to bubble free purified water while vortexing. TEC is next added and mixed for >30 minutes. Talc is slowly added and mixed to obtain homogenous dispersion. The coating desertion was next screened through 60-mesh sieve. The coating parameters are as follows (O'Hara Lab II-X 15"pna): inlet temp: 37-40° C.; outlet temp: 25-28° C.; air flow rate: 150-175 CFM; pan speed: 8-9 rpm; and spray distance: 6-8".

Tablets were next coated. The exhaust temperature and coating speed (weight change/minute) were first calibrated and tables were coated for a set amount of time. Tablets were allowed to roll for 3 minutes at a constant temperature (37-40° C.) and tablets were next cooled and transferred to a forced air oven (40° C.) for 24 hours to dry.

Example 13

Film-Coated Formulation

Film-coated tablets were formulated by coating a memantine tablet with or without an Opadry® subcoat and with a Surelease® overcoat. 2% Opadry® based coating with 2% Surelease® overcoat presented a desired release profile.

Example 14

Matrix Core Tablet

Matrix Core tablets were formulated as shown in the table below. (Appearance=good, weight=167 mg; hardness=5.1 kg; friability 100 revs: 0.6%). Low coating weight gain was associated with rapid hydration of coating, whereas high coating weight gain was associated with slow hydration of coating.

| | % w/w | mG/Tablet |
|---|---|---|
| Granulation | | |
| Memantine HCL | 14 | 22.5 |
| Avicel PH102 | 60 | 100.0 |
| Eudragit RS-30D | 15 | 25.6 |
| Extragranular | | |
| Methocel K100M* | 10 | 16.8 |
| Mg Stearate | 1 | 1.6 |
| Total | 100 | 166.5 |

Coated beads or granules were compressed into a tablet. A honeycomb-like structure is established during compression. The tablet disintegrates into beads and granules, whose individual properties then control release of memantine. A HPMC subcoat may optionally be used. Water penetrates the Surelease coating, which remains intact therefore trapping the HPMC subcoat between the core and the external coating. The water-soluble HPMC subcoating hydrates. While it is water soluble it is a large molecular weight polymer which cannot diffuse out through the water insoluble ethycellulose coating. Release of drug will not occur until water reaches the core. The delay should therefore vary as a function of the amount of HMPC in the tablet. Water reaches the outside surface of the core and memantine dissolves. High water solubility establishes a high concentration gradient. Dissolved memantine next diffuses through the hydrated HPMC layer and the porous ethylcellulose coating. Accordingly, a high level of ethylcellulose coating controls the release rate by the external coating whereas a lower level of ethylcellulose coating results in erosion, sloughing off of the hydrated HPMC, and the control of release being governed by the matrix bead.

Example 15

In Vitro Dissolution Profile of Sustained Release Formulations of Memantine Various sustained release formulations of memantine were prepared as follows.

Matrix Tablet Formulation 5001-6601

| Memantine HCL (22.5 mg) | 13.51% |
|---|---|
| Avicel PH102 | 60.04% |
| Eudragit RS-30D (30% w/w aqueous dispersion) | 15.37% |
| HPMC K100M | 10.08% |
| Magnesium Stearate | 1.00% |
| Total Component Weight | 166.5 mg |

Coated Tablet Formulation 5001-6701

| Memantine HCL (22.5 mg) | 13.21% |
|---|---|
| Avicel PH102 | 58.72% |
| Eudragit RS-30D (30% w/w aqueous dispersion) | 15.03% |
| HPMC K100M | 9.86% |
| Magnesium Stearate | 0.98% |
| Surelease ® Clear, (Formulation E-7-19010, Colorcon) | 2.20% |
| Total Component Weight | 170.2 mg |

Coated Tablet Formulation 5001-680

| | |
|---|---|
| Memantine HCL (22.5 mg) | 12.73% |
| Avicel PH102 | 56.55% |
| Eudragit RS-30D (30% w/w aqueous dispersion) | 14.48% |
| HPMC K100M | 9.50% |
| Magnesium Stearate | 0.94% |
| Opadry ® Clear, (Formulation YS-1-7006, Colorcon) | 3.00% |
| Surelease ® Clear, (Formulation E-7-19010, Colorcon) | 2.80% |
| Total Component Weight | 176.2 mg |

Coated Tablet Formulation 5001-6804

| | |
|---|---|
| Memantine HCL (22.5 mg) | 12.64% |
| Avicel PH102 | 55.98% |
| Eudragit RS-30D (30% w/w aqueous dispersion) | 14.33% |
| HPMC K100M | 9.40% |
| Magnesium Stearate | 0.93% |
| Opadry ® Clear, (Formulation YS-1-7006, Colorcon) | 3.00% |
| Surelease ® Clear, (Formulation E-7-19010, Colorcon) | 3.80% |
| Total Component Weight | 178 mg |

Coated Bead Formulation 5001-6990

| | |
|---|---|
| 20% Memantine HCL (22.5 mg) & Eudragit RS-30D (30% w/w aqueous dispersion) | 75% |
| Opadry ® Clear, (Formulation YS-1-7006, Colorcon) | 2.00% |
| Surelease ® Clear, (Formulation E-7-19010, Colorcon) | 10% |
| Total Component Weight | NA |

Coated Bead Formulation 5001-6991

| | |
|---|---|
| 20% Memantine HCL (22.5 mg) & Eudragit RS-30D (30% w/w aqueous dispersion) | 65% |
| Opadry ® Clear, (Formulation YS-1-7006, Colorcon) | 10.00% |
| Eudragit RS-30D coat (30% w/w aqueous dispersion) | 25% |
| Total Component Weight | NA |

Coated Bead Formulation 5001-6992

| | |
|---|---|
| 20% Memantine HCL (22.5 mg) & Eudragit RS-30D (30% w/w aqueous dispersion) | 55% |
| Opadry ® Clear, (Formulation YS-1-7006, Colorcon) | 10.00% |
| Eudragit RS-30D coat (30% w/w aqueous dispersion) | 35% |
| Total Component Weight | NA |

Coated Bead Formulation 5001-6993

| | |
|---|---|
| 20% Memantine HCL (22.5 mg) & Eudragit RS-30D (30% w/w aqueous dispersion) | 53% |
| Opadry ® Clear, (Formulation YS-1-7006, Colorcon) | 30.00% |
| Surelease ® Clear, (Formulation E-7-19010, Colorcon) | 17% |
| Total Component Weight | NA |

Exemplary in vitro dissolution profiles of sustained release formulations of memantine and Namenda are shown in FIGS. 2A-2C and 3A-3B. The dissolution profiles of the sustained release memantine formulations in neutral medium (FIG. 2A) are substantially identical to their dissolution profiles in an acidic dissolution medium (FIG. 2B).

FIG. 2C is a graph showing effect of medium on the release profile of memantine from matrix tablets. Testing was performed using the R&D method using Apparatus 2 at 50 RPM. Three media were employed: Vessels 1&2=Water; Vessels 3&4=pH 1.2 Buffer; Vessels 5&6=pH 1.2 Buffer for 2 hours, then pH adjusted to 6.8. There were no significant differences in the profiles for the first two hours or between the profile obtained in a pH 1.2 buffer and water. The switch to a buffer having a pH 6.8, however, slowed down release. Accordingly, optimal media testing may be water (pH of a solution containing approximately 22.5 mg Memantine HCl in water is 7.7, consistent with a dilute solution of a base that has a pKa of about 9-10).

Formulation of Memantine HCl SR Capsules as Coated Pellets (22.5 mg)

Memantine was formulated as shown in the table below.

| Ingredients | Qty/unit (mg) |
|---|---|
| Memantine Hydrochloride | 22.5 |
| HPMC 5 cps | 9.5 |
| Non-pareils (Celpheres) | 90.0 |
| Isopropyl alcohol | q.s. |
| Dichloromethane | q.s |
| Total | 122.0 |

The memantine pellets were next coated using a Wurster coater. The Ethylcellulose: HPMC ratios of coating formulation I and coating formulation II were 9:1 and 8:2, respectively (see table below).

| | % | |
|---|---|---|
| Ingredients | Coating Formula I | Coating Formula II |
| Ethylcellulose 7 cps | 8.10 | 6.46 |
| HPMC 5 cps | 0.92 | 1.61 |
| Miglyol 812 N | 0.42 | 0.32 |
| Isopropyl alcohol | 72.54 | 67.31 |
| Dichloromethane | 18.02 | 24.30 |
| Coating levels (%) | 8.7, 11.2, 13.0 & 16.5 | 8.0, 11.6, 14.4 & 16.11 |

Once coated, the memantine pellets were encapsulated by hand filling, such. Each capsule contained 22.5 mg of memantine. The capsule size was '3.'

The dissolution profiles of the above formulations were next determined with a USP II (Paddle) system, using water (500 mL) as a dissolution medium at 50 rpm. Different coating levels (% w/w) were employed. The release profile of each memantine capsule (22.5 mg) was determined at 1, 2, 4, 6, 8, and 12 hours (see tables below).

Release Data of Memantine HCl SR Capsules 22.5 mg Filled with Pellets Coated with Coating Formula I at Different Coating Levels (% w/w)

| Time (hours) | 8.70% | 11.20% | 13% | 16.50% |
|---|---|---|---|---|
| 0 | 0 | 0 | 0 | 0 |
| 1 | 11 | 8 | 6 | 4 |
| 2 | 34 | 23 | 18 | 11 |

-continued

| Time (hours) | 8.70% | 11.20% | 13% | 16.50% |
|---|---|---|---|---|
| 4 | 69 | 51 | 41 | 28 |
| 6 | 82 | 68 | 57 | 42 |
| 8 | 88 | 76 | 67 | 54 |
| 12 | 95 | 86 | 80 | 68 |

Release Data of Memantine HCl SR Capsules 22.5 mg Filled with Pellets Coated with Coating Formula II at Different Coating Levels (% w/w)

| Time (Hours) | 8% | 11.60% | 14.40% | 16.60% |
|---|---|---|---|---|
| 0 | 0 | 0 | 0 | 0 |
| 1 | 30 | 14 | 11 | 5 |
| 2 | 65 | 39 | 31 | 17 |
| 4 | 93 | 69 | 63 | 40 |
| 6 | 99 | 83 | 76 | 57 |
| 8 | 100 | 90 | 86 | 65 |
| 12 | 100 | 99 | 95 | 83 |

Drug release was sustained up to 12 hours, in a non-linear fashion. In most cases, pellets showed faster release after 2 hours. To linearise the release profile up to 12 hours with around 100% drug release, drug layering and coating compositions may be varied.

Example 16

Predicted Plasma Profile of Memantine Sustained Release

Using the formulations and dissolution profiles described in Example 14, the serum concentrations resulting from single or multiple administrations of memantine were calculated using the pharmacokinetic software, GastroPlus, from Simulations Plus (see FIG. 2D). The administration of either of the sustained release formulations achieves a therapeutically effective steady state serum concentration much sooner than with Namenda (13 days versus 30 days from the start of treatment therapy). Furthermore, the initial slope of the sustained release formulation is less than the slope obtained with the immediate release formulation.

Example 17

Patch Providing Extended Release of Memantine

As described above, extended release formulations of an NMDA antagonist may be formulated for topical administration. Memantine transdermal patch formulations may be prepared as described, for example, in U.S. Pat. Nos. 6,770,295 and 6,746,689, hereby incorporated by reference.

For the preparation of a drug-in-adhesive acrylate, 5 g of memantine is dissolved in 11 g of ethanol and is added to 20 g of Durotak 387-2287 (National Starch & Chemical, U.S.A.). The drug gel is coated onto a backing membrane (Scotchpak 1012; 3M Corp., U.S.A.) using a coating equipment (e.g., RK Print Coat Instr. Ltd, Type KCC 202 control coater). The wet layer thickness is 400 µm. The laminate is dried for 20 minutes at room temperature and then for 30 minutes at 40° C. A polyester release liner is laminated onto the dried drug gel. The sheet is cut into patches and stored at 2-8° C. until use (packed in pouches). The concentration of memantine in the patches ranges between 5.6 and 8 mg/cm$^2$.

Example 18

Patch Providing Extended Release of Memantine

A patch allowing the extended release of memantine may be prepared as follows. The matrix patch is composed of 1 mm thick polyolefin foam (as an occlusive backing) coated with an acrylate matrix that includes a mixture of memantine and an intradermal-penetration agent in an acrylate polymer. The matrix is prepared by mixing memantine (20 weight percent); acrylate polymer (Durotak® 387-2052, 75 weight percent); intradermal-penetration agent; aluminumacetylacetonate (Al(ACAC)$_3$, 0.4 weight percent, as a crosslinker); and ethanol until homogeneous. The homogeneous mixture is then coated on polyolefin foil with a hand-coater machine to an average thickness of about 270 µm. The coated foil is dried for about one hour at about 50° C. to evaporate the ethanol. The resulting patch weighs approximately 50 g/m$^2$ dry.

Example 19

Determination of Increased-Dose Tolerability for Memantine SR Formulations

A study to determine safety and tolerability of increased dosing for Memantine SR is described below. The study results are expected establish a maximum administerable dose greater than 20 mg when given once per day, as well as confirm tolerability of a non-dose escalating dosing regimen (i.e., administration of substantially identical doses of memantine throughout the term of dosing).

| Purpose | Multiple Dose Tolerability |
|---|---|
| Dosage: | 11.25, 22.5, 33.75, 45.0, 56.25, 67.5, 78.75 and 90.0 mg memantine SR |
| Concurrent Control: | Placebo |
| Route: | Oral |
| Subject Population: | Healthy, drug-naive male subjects |
| Structure: | Placebo-controlled, Sequential dose escalation in |
| Study Sites: | Single center |
| Blinding: | Open label |
| Method of Subject Assignment: | Subjects in each Cohort will be randomized to either active drug (n = 8-10) or placebo (n = 2) |
| Total Sample Size: | 80-100 subjects |
| Primary Efficacy Endpoint: | None |
| Adverse Events: | Monitored with reports by clinic personnel at least 2 or 3 times per day throughout the study, as well as volunteered by subjects. |
| Blood Collection | Blood sampling and plasma preparations at the following time points: Day 1: 0, 1, 2, 3, 4, 6, 7, 8, 10, 12, 14, 16, 20 Days 2-6: pre-dose trough Day 7: 0, 1, 2, 3, 4, 6, 7, 8, 10, 12, 14, 16, 20, 24, 48, 72, 96, 120, 144, and 168 hours |
| Analysis | Adverse events (including dizziness, headache, confusion, constipation, hypertension, coughing), tolerability, Pharmacokinetics |

Example 20

Determination of Increased-Dose Tolerability for Amantadine SR Formulations

A study to determine safety and tolerability of increased dosing for Amantadine SR is described below. The study results are expected establish a maximum administerable dose greater than 200 mg when given once per day, as well as confirm tolerability of a non-dose escalating dosing regimen (i.e., administration of substantially identical doses of memantine throughout the term of dosing).

| Purpose | Multiple Dose Tolerability |
|---|---|
| Dosage: | 100, 200, 300, 400, 500, 600, 700, and 800 mg amantadine SR |
| Concurrent Control: | Placebo |
| Route: | Oral |
| Subject Population: | Healthy, drug-naive male subjects |
| Structure: | Placebo-controlled, Sequential dose escalation |
| Study Sites: | Single center |
| Blinding: | Open label |
| Method of Subject Assignment: | Subjects in each Cohort will be randomized to either active drug (n = 8) or placebo (n = 2) |
| Total Sample Size: | 80-100 subjects |
| Primary Efficacy Endpoint: | None |
| Adverse Events: | Monitored with reports by clinic personnel at least 2 or 3 times per day throughout the study, as well as volunteered by subjects. |
| Blood Collection | Blood sampling and plasma preparations at the following time points: Day 1: 0, 1, 2, 3, 4, 6, 7, 8, 10, 12, 14, 16, 20 Days 2-6: pre-dose trough Day 7: 0, 1, 2, 3, 4, 6, 7, 8, 10, 12, 14, 16, 20, 24, 48, 72, 96, 120, 144, and 168 hours |
| Analysis | Adverse events (including dizziness, headache, confusion, constipation, hypertension, coughing), tolerability, Pharmacokinetics |

Example 21

Treating NMDA-Receptor Related Disorders with Controlled Release Formulations

A patient diagnosed with dementia of the Alzheimer's type is administered 22.5 mg of memantine in a sustained release formulation (e.g., formulated as described in Example 13) once a day. Memantine plasma concentrations can be determined using HPLC coupled to mass spectrometric detection as described in Periclou et al., Annals of Pharmacotherapy 38:1389-94 (2004). A therapeutically effective steady state serum concentration is reached within ten days of the start of this therapy.

Example 22

Treating Major Depression

A patient diagnosed with Major Depression is administered 22.5 mg or more, up to a maximum tolerated dose (as determined using the protocol in Example 20) of memantine formulated as described in Example 13, once daily. A therapeutically effective steady state serum concentration is reached within ten days of the start of this therapy.

Example 23

Treating Dyskinesia in Patients with Parkinson's Disease

A Parkinson's patient experiencing dyskinesia is administered a daily dose of 400 mg of a sustained released amantadine formulation. Improvements in dyskinesia are measured using UPDRS scoring.

Example 24

Clinical Trial to Compare Memantine SR Formulation to Namenda® in Patients with Alzheimer's Disease or Refractory Depression

| Protocol Objective: | Confirm the improvement in onset to efficacy for a QD, non-dose escalating treatment regimen |
|---|---|
| Inclusion Criteria: | Chosen from the following indications: Alzheimer's - moderate to severe AD patients (see Tariot et al., JAMA 291: 317-24 (2004)) Refractory depression/MADD - unresponsive to SSRIs, HamD 20-24. (see Mann N Engl J Med 353: 1819-34 (2005), Berman Biol Psychiatry 47: 351-4 (2000), Gauthier et al., Int J Geriatr Psychiatry 20, 459-64 (2005)) |
| Dosage: | 22.5 mg (20 mg delivered) Memantine SR given once per day from the onset of therapy; |
| Concurrent Control: | 10 mg Memantine IR given twice per day after manufacturer's recommended dose escalation |
| Route: | Orally or transdermally |
| Blinding: | Double blinding |
| Total Sample Size: | 120 patients and 120 controls for each indication group |
| Primary Efficacy Endpoint: | HAMD, MADRS, NPI measured at weekly visits |
| Secondary Efficacy Endpoint: | Fatigue |

In each of the above active controlled, double blind trial, the time required to reach a steady state plasma therapeutic level for Memantine SR is compared to that of memantine IR. Patients are screened against the inclusion criteria and admitted to the trial population. After a 4 week washout of interfering medications, patients are scored at baseline and administered the test medication in a blinded fashion using an over-encapsulation procedure. Measurements of the endpoints are made at weekly intervals on each patient.

Based on our computer simulations, patients receiving a full dose of Memantine SR are expected to reach steady state in 8 days, rather than the 40 days required in patients being administered memantine IR. Thus, beneficial effects are expected earlier in their treatment course.

Example 25

Clinical Trial to Assess Efficacy of Amantadine SR Formulation in Patients with Multiple Sclerosis

| Protocol Objective: | Confirm the improvement in depression, neuropsychiatric complications, and fatigue for a QD, non-dose escalating treatment regimen of amantadine |
|---|---|

-continued

| | |
|---|---|
| Inclusion Criteria: | MS - relapsing/remitting on interferon treatment with concomitant fatigue (see Bashki et al., Mult Scler 6: 181-5 (2000), Siegert et al., J Neurol Neurosurg Psychiatry 76: 469-75 (2005)) |
| Dosage: | 400 mg Amantadine SR given once per day from the onset of therapy. |
| Concurrent Control: | Placebo |
| Route: | Orally |
| Blinding: | Double blinding |
| Total Sample Size: | 40 patients and 40 controls |
| Primary Efficacy Endpoint: | HAMD, MADRS, NPI measured at weekly visits |
| Secondary Efficacy Endpoint: | Fatigue |

In each of the above active controlled, double blind trial, Amantadine SR is compared to placebo to measure the effect. Patients are screened against the inclusion criteria and admitted to the trial population. After a 4 week washout of interfering medications, patients are scored at baseline and administered the test medication in a blinded fashion using an overcapsulation procedure. Measurements of the endpoints are made at weekly intervals on each patient.

Patients receiving the Amantadine SR are expected to show an improved score in the test criteria correlating to an improvement in depression or fatigue.

Example 26

Clinical Trial to Assess Efficacy of Amantadine SR Formulation in Patients with Drug Induced Dyskinesia

| | |
|---|---|
| Title: | High Dose Amantadine for the treatment of Drug-Induced Dyskinesia |
| Study Phase: | II |
| Purpose | This study will evaluate the effects of amantadine on Parkinson's disease symptoms and on dyskinesias (involuntary movements) that develop as a result of long-term levodopa treatment. Amantadine inhibits the activity of glutamate which is thought to be elevated in patients with Parkinson's disease. The study objective is to test the hypothesis that blockade of glutamate receptors by high doses of amantadine will lessen the severity of Parkinsonian signs and levodopa-associated motor response complications in PD patients to a greater extent than current amantadine doses and dose forms. |
| Name of Drug: | Amantadine SR |
| Dosage: | 400 mg QD |
| Concurrent Control: | Symmetrel (amantadine immediate release) |
| Route: | Oral |
| Subject Population: | Patients with relatively advanced Parkinson's disease and dyskinesias who are between 30 and 80 years of age having a URPDS-3 score of between 16 and 20. Candidates are screened with a complete medical history and physical examination, neurological evaluation, blood and urine tests, and electrocardiogram (ECG). |
| Structure: | Two arm study, treatment and placebo arms. |
| Study Sites: | Multiple |
| Blinding: | Double blind |
| Method of Subject Assignment: | Random |
| Total Sample Size: | 40 patients per arm |
| Study Term | Two weeks |

-continued

| | |
|---|---|
| Primary Efficacy Endpoint: | Parkinsonian symptoms and choreiform dyskinesias are scored every 10 minutes by a masked neurologist using an abbreviated UPDRS-3 rating scale. A modified abnormal movement scale (AIMS) describing involuntary movements in all extremities and trunk and face on a scale from 1-4. |
| Secondary Efficacy Endpoints: | Efficacy is assessed using validated motor function scales. Safety is monitored by means of frequent clinical evaluations and laboratory tests. |
| Adverse Events: | Standard battery of AE assessments collected throughout study period |
| Blood Collection: | To determine blood levels of amantadine, samples are drawn intermittently throughout the study. |
| Analysis: | Standard assays to determine concentration of amantadine in blood samples. |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of administering memantine to a human subject in need thereof, comprising:
orally administering to the subject once per day over multiple days a sustained release oral dosage form comprising memantine or a pharmaceutically acceptable salt thereof and a component that sustains release of the memantine or the salt thereof;
wherein a daily dose of 12.5 to 40 mg of memantine or pharmaceutically acceptable salt thereof is administered from the initiation of therapy without prior dose escalation of memantine;
wherein such administration results in the subject achieving a therapeutically effective steady state memantine plasma concentration within 20 days after initiation of therapy with said dosage form; and
wherein the subject has a condition selected from the group consisting of Alzheimer's disease, dementia, Parkinson's disease and neuropathic pain.

2. The method of claim 1, wherein said sustained release memantine provides a change in plasma concentration as a function of time (dC/dT) in a defined time period of 0 to 6 hours after administration as measured in a single dose human PK study, that is less than about 50% of the dC/dT provided by the same quantity of an immediate release form of memantine in said defined time period.

3. The method of claim 1, wherein said sustained release memantine provides a change in plasma concentration as a function of time (dC/dT) that is less than about 50% of the dC/dT provided by the same quantity of an immediate release form of memantine, wherein the dC/dT is measured in a single dose human PK study between the time period of 0 to Tmax of the immediate release form of memantine.

4. The method of claim 1, wherein the dosage form has a memantine in vitro dissolution profile ranging between 0.1-20% in one hour, 5-30% in two hours, 40-80% in six hours, and 50 to 90% in 10 hours, wherein the dissolution profile is determined using a USP type 2 (paddle) dissolution system at 50 rpm, at a temperature of 37±0.5° C., in 500 ml water.

5. The method of claim 1, wherein said subject has not been administered memantine or a pharmaceutically acceptable salt thereof within one week prior to the initiation of therapy with said sustained release oral dosage form.

6. A method of administering memantine to a human subject in need thereof, comprising:

orally administering to the subject once per day over multiple days a sustained release oral dosage form comprising memantine or a pharmaceutically acceptable salt thereof and a component that sustains release of the memantine or the salt thereof;

wherein 12.5 to 40 mg of memantine or pharmaceutically acceptable salt thereof is administered daily from the initiation of therapy without prior dose escalation of memantine;

wherein daily administration of 12.5 to 40 mg of memantine or pharmaceutically acceptable salt thereof results in the subject achieving a therapeutically effective steady state memantine plasma concentration within 20 days after initiation of therapy with said dosage form; and wherein the subject has a condition selected from the group consisting of Alzheimer's disease, dementia, Parkinson's disease and neuropathic pain.

7. The method of claim 6, wherein said sustained release memantine provides a change in plasma concentration as a function of time (dC/dT) in a defined time period of 0 to 6 hours after administration as measured in a single dose human PK study, that is less than about 50% of the dC/dT provided by the same quantity of an immediate release form of memantine in said defined time period.

8. The method of claim 6, wherein said sustained release memantine provides a change in plasma concentration as a function of time (dC/dT) that is less than about 50% of the dC/dT provided by the same quantity of an immediate release form of memantine, wherein the dC/dT is measured in a single dose human PK study between the time period of 0 to Tmax of the immediate release form of memantine.

9. The method of claim 6, wherein the dosage form has a memantine in vitro dissolution profile ranging between 0.1-20% in one hour, 5-30% in two hours, 40-80% in six hours, and 50 to 90% in 10 hours, wherein the dissolution profile is determined using a USP type 2 (paddle) dissolution system at 50 rpm, at a temperature of 37±0.5° C., in 500 ml water.

10. The method of claim 6, wherein said subject has not been administered memantine or a pharmaceutically acceptable salt thereof within one week prior to the initiation of therapy with said sustained release oral dosage form.

* * * * *